US010422452B2

(12) United States Patent
Graham et al.

(10) Patent No.: US 10,422,452 B2
(45) Date of Patent: Sep. 24, 2019

(54) HIGH PRESSURE FLUIDIC CONNECTION ASSEMBLIES

(71) Applicant: IDEX Health & Science LLC, Oak Harbor, WA (US)

(72) Inventors: Craig Graham, Anacortes, WA (US); Don Pein, Oak Harbor, WA (US)

(73) Assignee: IDEX Health & Sciences LLC, Oak Harbor, WA (US)

( * ) Notice: Subject to any disclaimer, the term of this patent is extended or adjusted under 35 U.S.C. 154(b) by 514 days.

(21) Appl. No.: 14/686,642

(22) Filed: Apr. 14, 2015

(65) Prior Publication Data

US 2015/0300542 A1   Oct. 22, 2015

Related U.S. Application Data

(60) Provisional application No. 61/980,331, filed on Apr. 16, 2014.

(51) Int. Cl.

| B01L 3/00 | (2006.01) |
|---|---|
| F16L 21/00 | (2006.01) |
| B01D 15/10 | (2006.01) |
| G01N 30/60 | (2006.01) |
| F16L 19/02 | (2006.01) |
| F16L 33/22 | (2006.01) |
| G01N 30/02 | (2006.01) |

(52) U.S. Cl.
CPC ............ *F16L 21/007* (2013.01); *B01D 15/10* (2013.01); *F16L 19/0206* (2013.01); *F16L 19/0212* (2013.01); *F16L 33/224* (2013.01); *G01N 30/6004* (2013.01); *G01N 30/6026* (2013.01); *F16L 19/0243* (2013.01); *F16L 2201/44* (2013.01); *G01N 2030/027* (2013.01)

(58) Field of Classification Search
CPC .......... B01L 3/561; B01L 3/563; B01L 3/565; F16L 15/04; F16L 47/06; F16L 47/065; F16L 47/08; F16L 47/10; G01N 30/6026
See application file for complete search history.

(56) References Cited

U.S. PATENT DOCUMENTS

| 2,017,493 | A | 10/1935 | Glowacki |
|---|---|---|---|
| 4,529,230 | A | 7/1985 | Fatula |
| 4,776,618 | A | 10/1988 | Barree |
| 5,217,261 | A | 6/1993 | Dewitt et al. |
| 5,324,427 | A * | 6/1994 | Traveset-Masanes ....... G01N 30/6039 210/198.2 |
| 5,472,598 | A | 12/1995 | Schick |
| 5,525,303 | A | 6/1996 | Ford et al. |
| 5,621,191 | A | 4/1997 | Norris et al. |
| 5,669,637 | A | 9/1997 | Chitty et al. |
| 5,730,943 | A | 3/1998 | Ford et al. |
| 6,095,572 | A | 8/2000 | Ford et al. |
| 7,100,948 | B2 | 9/2006 | Guest |
| 7,144,502 | B2 | 12/2006 | Fermier et al. |

(Continued)

OTHER PUBLICATIONS

International Search Report dated Aug. 14, 2015.

*Primary Examiner* — Jill A Warden
*Assistant Examiner* — Dwayne K Handy
(74) *Attorney, Agent, or Firm* — Vinson & Elkins LLP

(57) ABSTRACT

Fluidic connection assemblies, ports, unions and other components are provided that are well-suited for use in HPLC and UHPLC, as well as in other analytical instrument systems. Such assemblies, ports, unions and components can be biocompatible.

31 Claims, 31 Drawing Sheets

(56) References Cited

U.S. PATENT DOCUMENTS

| | | |
|---|---|---|
| 7,311,502 B2 | 12/2007 | Gerhardt et al. |
| 8,173,070 B2 | 5/2012 | Gerhardt et al. |
| 8,201,854 B2 | 6/2012 | Ford et al. |
| 8,573,653 B2 | 11/2013 | Gamache |
| 2012/0224411 A1 | 2/2012 | Hahn et al. |
| 2012/0223522 A1 | 9/2012 | Graham |

* cited by examiner

HIGH PRESSURE FLUIDIC CONNECTION ASSEMBLIES

CROSS-REFERENCE TO RELATED APPLICATION

This application claims benefit of priority to U.S. Provisional Application No. 61/980331, filed Apr. 16, 2014.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This disclosure relates generally to fluidic assemblies for use in ion chromatography, liquid chromatography and other analytical systems, and relates more particularly to fluidic assemblies well-suited for use in high pressure and ultra-high pressure liquid chromatography.

2. Description of the Related Art

Liquid chromatography (LC) and ion chromatography (IC) are well-known techniques for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector. The detector detects the presence of specific molecules or compounds. Two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample. Additionally, LC systems may utilize mass spectrometric detection for identification and quantification of the sample, either in addition to, or as an alternative to, the conventional detectors described previously. Ion chromatography relies on the detection of ions in solution, so most metallic materials in the flow path can create interference in the detection scheme, as they create background ions.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, and then connect a supply of the selected mobile phase and a selected column to the LC system before operation. In order to be suitable for high performance liquid chromatography (HPLC) applications, each connection must be able to withstand the typical operating pressures of the HPLC system. If the connection is too weak, it may leak. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections, especially in HPLC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples, and cannot be routinely used for ion chromatography. For example, the components in a sample may attach themselves to the wall of stainless steel tubing. This presents problems because the detector's measurements (and thus the chromatogram) of a given sample may not accurately reflect the sample if some of the sample's components or ions remain in the tubing and do not pass the detector. Perhaps of even greater concern, however, is the fact that ions from the stainless steel tubing may detach from the tubing and flow past the detector, thus leading to potentially erroneous results. Hence, there is a need for biocompatible or metal-free connections through the use of a material that is chemically inert with respect to such "biological" samples and the mobile phase used with such samples, so that ions will not be released by the tubing and thus contaminate the sample.

In many applications using selector/injector valves to direct fluid flows, and in particular in liquid chromatography, the volume of fluids is small. This is particularly true when liquid chromatography is being used as an analytical method as opposed to a preparative method. Such methods often use capillary columns and are generally referred to as capillary chromatography. In capillary chromatography, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less. In general, and especially with such small sample sizes and such flow rates, it is important to provide connections that do not introduce any additional dead volume, or that minimize dead volume, into the system.

Most conventional HPLC systems include pumps which can generate relatively high pressures of up to around 5,000 psi to 6,000 psi or so. In many situations, an operator can obtain successful results by operating a LC system at "low" pressures of anywhere from just a few psi or so up to 1,000 psi or so. More often than not, however, an operator will find it desirable to operate a LC system at relatively "higher" pressures of over 1,000 psi.

Another, relatively newer liquid chromatography form is Ultra High Performance Liquid Chromatography (UHPLC) in which system pressure extends upward to 1400 bar or 20,000 psi. Both HPLC and UHPLC are examples of analytical instrumentation that utilize fluid transfer at elevated pressures. For example, in U.S. Pat. No. 8,173,070, an injection system is described for use with UHPLC applications, which are said to involve pressures in the range from 20,000 psi to 120,000 psi. In U.S. Pat. No. 7,311,502, the use of a hydraulic amplifier is described for use in UHPLC systems involving pressures in excess of 25,000 psi. In U.S. Pat. No. 7,144,502, a system for performing UHPLC is disclosed, with UHPLC described as involving pressures above 5,000 psi (and up to 60,000 psi). Applicants hereby incorporate by reference as if fully set forth herein U.S. Pat. Nos. 7,311,502, 8,173,070 and 7,144,502.

As noted, liquid chromatography (as well as other analytical) systems, including HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the HPLC column itself; and a detector that analyzes the carrier fluid as it leaves the column. Ion chromatography may also utilize a suppressor column to facilitate detection dynamic range. These various components may typically be connected by a miniature fluid conduit, or tubing, such as metallic or polymeric tubing (for ion chromatography), usually having an internal diameter of 0.003 to 0.040 inch.

All of these various components and lengths of tubing are typically interconnected by threaded fittings. Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. Although a wrench or wrenches may be used, other tools such as pliers or other gripping and holding tools are sometimes used. In addition, the use of such approaches to connect components of an UHPLC system often results in deformation or swaging of a ferrule used to provide a leak proof seal of tubing to a fitting or component. This often means that the ferrule and tubing connection, once made, cannot be reused without a risk of introducing dead volumes into the system. In addition, such approaches may involve crushing or deformation of the inner diameter of the tubing, which may adversely affect the flow characteristics and the pressures of the fluid within the tubing. While hand-tightened threaded fittings eliminate the need for wrenches or other tools, these fittings typically cannot stand up to the extreme pressures of HPLC or UHPLC.

Another approach to provide a connection in an UHPLC system involves providing a fitting assembly that uses a combination of components, including two separate ferrules. Such an approach is considered undesirable because by requiring two places for the ferrules to provide leak proof seals, it provides two places where the fluid to be analyzed may leak, as well as where dead volumes may be provided. In addition, this approach involves the use of additional components, which can cost more and also increase the time and effect to assemble them to make a connection or disassemble them when disconnecting tubing from a component or other fitting assembly.

It will be understood by those skilled in the art that, as used herein, the term "LC system" is intended in its broad sense to include all apparatus and components in a system used in connection with liquid chromatography, whether made of only a few simple components or made of numerous, sophisticated components which are computer controlled or the like. Those skilled in the art will also appreciate that an LC system is one type of an analytical instrument (AI) system. For example, gas chromatography is similar in many respects to liquid chromatography, but obviously involves a gas sample to be analyzed. Although the following discussion focuses on liquid chromatography, those skilled in the art will appreciate that much of what is said also has application to other types of AI systems and methods.

Therefore, it is an object of the present disclosure to provide fluidic connection assemblies, such as assemblies, ports and unions, for use in a HPLC or an UHPLC system.

It is another object of the present disclosure to provide fluidic connection assemblies that can hold to about 18,000 pounds per square inch ("psi") or more, and be reusable about 10 times or more.

It is another object of the present disclosure to provide fluidic connection assemblies that can be quickly disconnected or connected by an operator to a HPLC or an UHPLC system.

It is another object of the present disclosure to provide fluidic connection assemblies for use in a HPLC or an UHPLC system that are biocompatible.

It is yet another object of the present disclosure to provide fluidic connection assemblies for use in a HPLC or an UHPLC system that have a lower cost than currently existing fluidic connection assemblies.

It is yet another object of the present disclosure to provide captivated fluidic connection assemblies for use in a HPLC or an UHPLC system.

It is still another object of the present disclosure to provide fluidic connection assemblies that require relatively low torque values (1.5 to 2.0 in-ib) for use in a HPLC or an UHPLC system and therefore do not require tools to connect and disconnect.

It is still another object of the present disclosure to provide pre-made fluidic connection assemblies for use in a HPLC or an UHPLC system.

The above and other advantages of the present disclosure will become readily apparent to those skilled in the art from the following detailed description of the present disclosure, and from the attached drawings, which are briefly described below.

SUMMARY OF THE INVENTION

The present disclosure overcomes one or more of the deficiencies of the prior art by providing fluidic connection assemblies that are well-suited for use in AI and LC systems, and are particularly well-suited in some embodiments for use in high pressure and ultra high pressure liquid chromatography systems, such as HPLC and UHPLC.

The present disclosure provides a connection assembly or fitting for use in an analytical instrument system, comprising a nut having a first end and a second end and a passageway therethrough, a nut head proximal to the first end of the nut, an externally non-threaded portion, and an externally threaded portion, a locktube having a first end and a second end and a passageway therethrough, at least a first internal non-tapered portion and an internal tapered portion; the first end of the locktube adapted to engage the second end of the nut, and a ferrule having a first end, a second end, a passageway therethrough, and an external tapered portion, wherein the external tapered portion of the ferrule is adapted to securely engage with the internal tapered portion of the locktube. In certain embodiments the nut head is a hexagonal nut head, a knurled nut head, or a nut head that comprises a plurality of splines. In various embodiments the angle of the internal tapered portion of the locktube is between about 3° and 12° included angle, and therefore in particular embodiments the angle of the internal tapered portion of the locktube is about 3°, about 4°, about 5°, about 6°, about 7°, about 8°, about 9°, about 10°, about 11°, or about 12° included angle. In other embodiments the angle of the external tapered portion of the ferrule is between about 2° and 11° included angle, and therefore in certain embodiments the angle of the external tapered portion of the ferrule is about 2°, about 3°, about 4°, about 5°, about 6°, about 7°, about 8°, about 9°, about 10°, about 11°, or about 12° included angle. In some embodiments the angle of the internal tapered portion of the locktube and the external tapered portion of the ferrule are about equal included angles.

In additional embodiments, the locktube further comprises at least a second lip and at least a third non-tapered portion proximal to the second end of the locktube. In various of these embodiments the angle of the internal tapered portion of the locktube is between about 4° and 14° included angle, and therefore in particular embodiments the angle of the internal tapered portion of the locktube is about 4°, about 5°, about 6°, about 7°, about 8°, about 9°, about 10°, about 11°, about 12°, about 13°, or about 14° included angle. In other embodiments the ferrule further comprises an external protrusion proximal the second end of the ferrule. In certain of these embodiments the ferrule further comprises an external radius or arc between the external tapered portion and the external protrusion, and an internal lip. In various of these embodiments the angle of the external tapered portion of the ferrule is between about 2° and 12° included angle, and therefore in certain embodiments the angle of the external tapered portion of the ferrule is about 2°, about 3°, about 4°, about 5°, about 6°, about 7°, about 8°, about 9°, about 10°, about 11°, or about 12° included angle. In further embodiments the angle of the internal tapered portion of the locktube and the external tapered portion of the ferrule are about equal included angles.

In some embodiments the connection assembly further comprises a washer between the nut and the locktube, the washer having a passageway therethrough. In other embodiments at least a portion of the nut, the locktube, the ferrule and/or the washer is biocompatible. In still other embodiments the nut, the locktube, the ferrule and/or the washer comprises a metal, such as stainless steel, or can comprise a polymer, such as a polyaryletherketone (PAEK), including, but not limited to, polyetherketone (PEK), polyetheretherketone (PEEK™), polyetherketoneketone (PEKK), polyetheretherketoneketone (PEEKK), and polyetherketoneetherketoneketone (PEKEKK), or any combination thereof. In certain embodiments each of the components of the connection assembly can comprise the same material, or some or all of the components can comprise different materials. In additional embodiments the connection assembly further comprises at least one tube extending through the passageways of the nut, the locktube, the ferrule and/or the washer. In certain such embodiments the ferrule contacts the tube without substantially deforming the tube. In further embodiments the analytical instrument system comprises a liquid chromatography system, an ultra high pressure liquid chromatography system or an ultra high performance liquid chromatography system.

The present disclosure additionally provides a connection assembly for use in an analytical instrument system, comprising a nut having a first end and a second end and a passageway therethrough, a nut head proximal to the first end of the nut, an externally non-threaded portion, and an externally threaded portion, wherein the passageway of the nut comprises a lip and a wider portion proximal the second end of the nut, a locktube having a first end and a second end and a passageway therethrough, at least a first internal non-tapered portion and an internal tapered portion, the first end of the locktube adapted to be disposed in the wider portion of the passageway and engage the lip of the passageway, and a ferrule having a first end, a second end, a passageway therethrough, and an external tapered portion, wherein the external tapered portion of the ferrule is adapted to securely engage with the internal tapered portion of the locktube. In certain embodiments the analytical instrument system comprises a liquid chromatography system, an ultra high pressure liquid chromatography system or an ultra high performance liquid chromatography system. In other embodiments at least a portion of the nut, the locktube or the ferrule is biocompatible.

The present disclosure further provides a tube assembly for use in an analytical instrument system, comprising a nut having a first end and a second end and a passageway therethrough, a nut head proximal to the first end of the nut, an externally non-threaded portion, and an externally threaded portion, a locktube having a first end and a second end and a passageway therethrough, an internal non-tapered portion and an internal tapered portion, the first end of the locktube adapted to engage the second end of the nut, a ferrule having a first end, a second end, a passageway therethrough, and an external tapered portion, wherein the external tapered portion of the ferrule is adapted to securely engage with the internal tapered portion of the locktube, and a tube having a first end and a second end extending through the passageways of the nut, the locktube and the ferrule. In certain embodiments the ferrule further comprises an external protrusion proximal the second end of the ferrule. In various embodiments the tube comprises a metal, including, but not limited to, stainless steel, a polymer, including, but not limited to, polyetheretherketone, fused silica, or any combination thereof. In yet other embodiments the locktube further comprises at least a second internal non-tapered portion, and at least a first lip between the at least a first internal non-tapered portion and the at least a second internal non-tapered portion. In such embodiments the locktube can further comprise at least a second lip and at least a third non-tapered portion proximal to the second end of the locktube. In additional embodiments the tube assembly further comprises a washer between the nut and the locktube, the washer defining a passageway.

In still additional embodiments the tube assembly further comprises a second nut having a first end and a second end and a passageway therethrough, a nut head proximal to the first end of the second nut, an externally non-threaded portion, and an externally threaded portion, a second locktube having a first end and a second end and a passageway therethrough, an internal non-tapered portion and an internal tapered portion, the first end of the locktube adapted to engage the second end of the nut, and a second ferrule having a first end, a second end and a passageway therethrough, an external tapered portion, and an external protrusion proximal the second end, wherein the external tapered portion of the ferrule is adapted to securely engage with the internal tapered portion of the locktube, wherein the second nut, the second locktube and the second ferrule are proximal to the first end of the tube and the second nut, the second locktube and the second ferrule are proximal to the second end of the tube. In other embodiments the tube assembly further comprises a second washer between the second nut and the second locktube, the second washer defining a passageway therethrough. In various embodiments the second locktube further comprises at least a second internal non-tapered portion, and at least a first lip between the at least a first internal non-tapered portion and the at least a second internal non-tapered portion. In certain such embodiments the second locktube further comprises at least a second lip and at least a third non-tapered portion proximal to the second end of the second locktube. In yet other embodiments the second ferrule further comprises an external protrusion proximal the second end of the second ferrule. In some of these embodiments the second ferrule further comprises an external radius between the external tapered portion and the external protrusion, and an internal lip. In certain embodiments the analytical instrument system comprises a liquid chromatography system, an ultra high pressure liquid chromatography system or an ultra high performance liquid chromatography system. In further embodiments at least a portion of the nut and/or the second nut, the locktube and/or the second locktube, the ferrule and/or the second locktube, and/or the washer and/or the second washer is biocompatible.

The present disclosure further provides a port for use in an analytical instrument system, comprising a first end, a second end, a passageway therethrough, an internally threaded portion having a first end and a second end, an internal tapered portion proximal the second end of the internally threaded portion, and an internal face proximal the second end of the port. In certain embodiments the port further comprises a first internal non-tapered portion between the internally threaded portion and the internal tapered portion. In additional embodiments the port further comprises a second internal non-tapered portion between the internal tapered portion and the internal face. In various embodiments the port has a depth of less than 0.4 inches, and therefore in certain such embodiments the port has a depth of about 0.35 inches, about 0.3 inches, about 0.25 inches, about 0.2 inches, about 0.15 inches, about 0.132 inches, or about 0.13 inches. In other embodiments the port can operate at a pressure of about 18,000 pounds per square inch. In further embodiments the analytical instrument system comprises a liquid chromatography system, an ultra high pressure liquid chromatography system or an ultra high performance liquid chromatography system. In some embodiments at least a portion of the port is biocompatible.

The present disclosure additionally provides a union for use in an analytical instrument system, comprising a first end, a second end, a passageway therethrough, a first internally threaded portion, a first internal non-tapered portion, and a first internal tapered portion proximal to the first end of the union, and a second internally threaded portion, a second internal non-tapered portion, and a second internal tapered portion proximal to the second end of the union. In certain embodiments the union has a length of less than about 0.4 inches, and therefore in some embodiments the union has a length of about 0.38 inches, about 0.36 inches, about 0.35 inches, about 0.34 inches, about 0.32 inches, or about 0.30 inches. In various embodiments the union can operate at a pressure of about 18,000 pounds per square inch. In other embodiments the analytical instrument system comprises a liquid chromatography system, an ultra high pressure liquid chromatography system or an ultra high performance liquid chromatography system. In yet other embodiments at least a portion of the union is biocompatible. In further embodiments the union is adapted to securely receive a first connection assembly and a second connection assembly, wherein the first connection assembly and the second connection assembly form a seal with each other.

These and other embodiments and advantages of the disclosed connection assemblies are described below.

DETAILED DESCRIPTION

Figure 1:
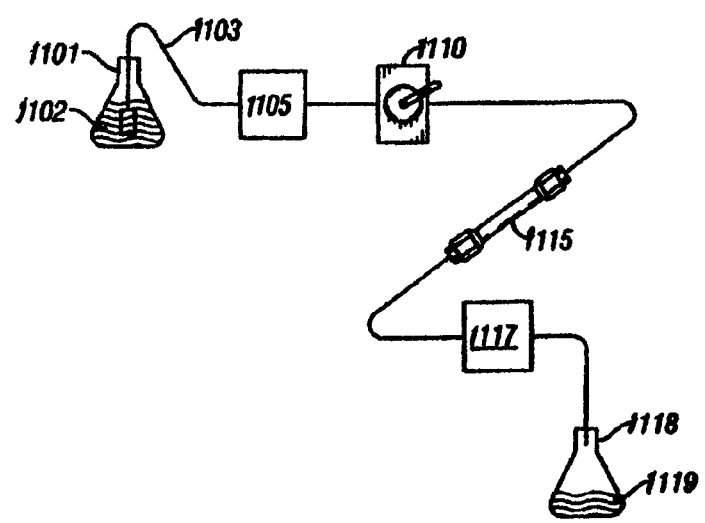
FIG. 1 is a block diagram of a conventional liquid chromatography system.

In FIG. 1, a block diagram of the essential elements of a conventional liquid chromatography (LC) system is provided. A reservoir 1101 contains a solvent or mobile phase 1102. Tubing 1103 connects the mobile phase 1102 in the reservoir 1101 to a pump 1105. The pump 1105 is connected to a sample injection valve 1110 which, in turn, is connected via tubing to a first end of a guard column (not shown). The second end of the guard column (not shown) is in turn connected to the first end of a primary column 1115. The second end of the primary column 1115 is then connected via tubing to a detector 1117. After passing through the detector 1117, the mobile phase 1102 and the sample injected via injection valve 1110 are expended into a second reservoir 1118, which contains the chemical waste 1119. As noted above, the sample injection valve 1110 is used to inject a sample of a material to be studied into the LC system. The mobile phase 1102 flows through the tubing 1103 which is used to connect the various elements of the LC system together.

When the sample is injected via sample injection valve 1110 in the LC system, the sample is carried by the mobile phase through the tubing into the column 1115. As is well known in the art, the column 1115 contains a packing material which acts to separate the constituent elements of the sample. After exiting the column 1115, the sample (as separated via the column 1115) then is carried to and enters a detector 1117, which detects the presence or absence of various chemicals. The information obtained by the detector 1117 can then be stored and used by an operator of the LC system to determine the constituent elements of the sample injected into the LC system. Those skilled in the art will appreciate that FIG. 1 and the foregoing discussion provide only a brief overview of a simplistic LC system that is conventional and well-known in the art, as is shown and described in U.S. Pat. No. 5,472,598, which is hereby incorporated by reference as if fully set forth herein. Those skilled in the art will also appreciate that while the discussion herein focuses on a LC system, other analytical systems can be used in connection with various embodiments of the disclosure, such as a mass spectrometry, microflow chromatography, nanoflow chromatography, nano-scale liquid chromatography, capillary electrophoresis, or reverse-phase gradient chromatography system.

Preferably, for an LC system to be biocompatible, the various components (except where otherwise noted) that may come into contact with the effluent or sample to be analyzed are made of a biocompatible material, such as the synthetic polymer polyetheretherketone, which is commercially available under the trademark PEEK™ from VICTREX®. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces. Those skilled in the art will appreciate that other polymers may be desirable in certain applications.

Figure 2:
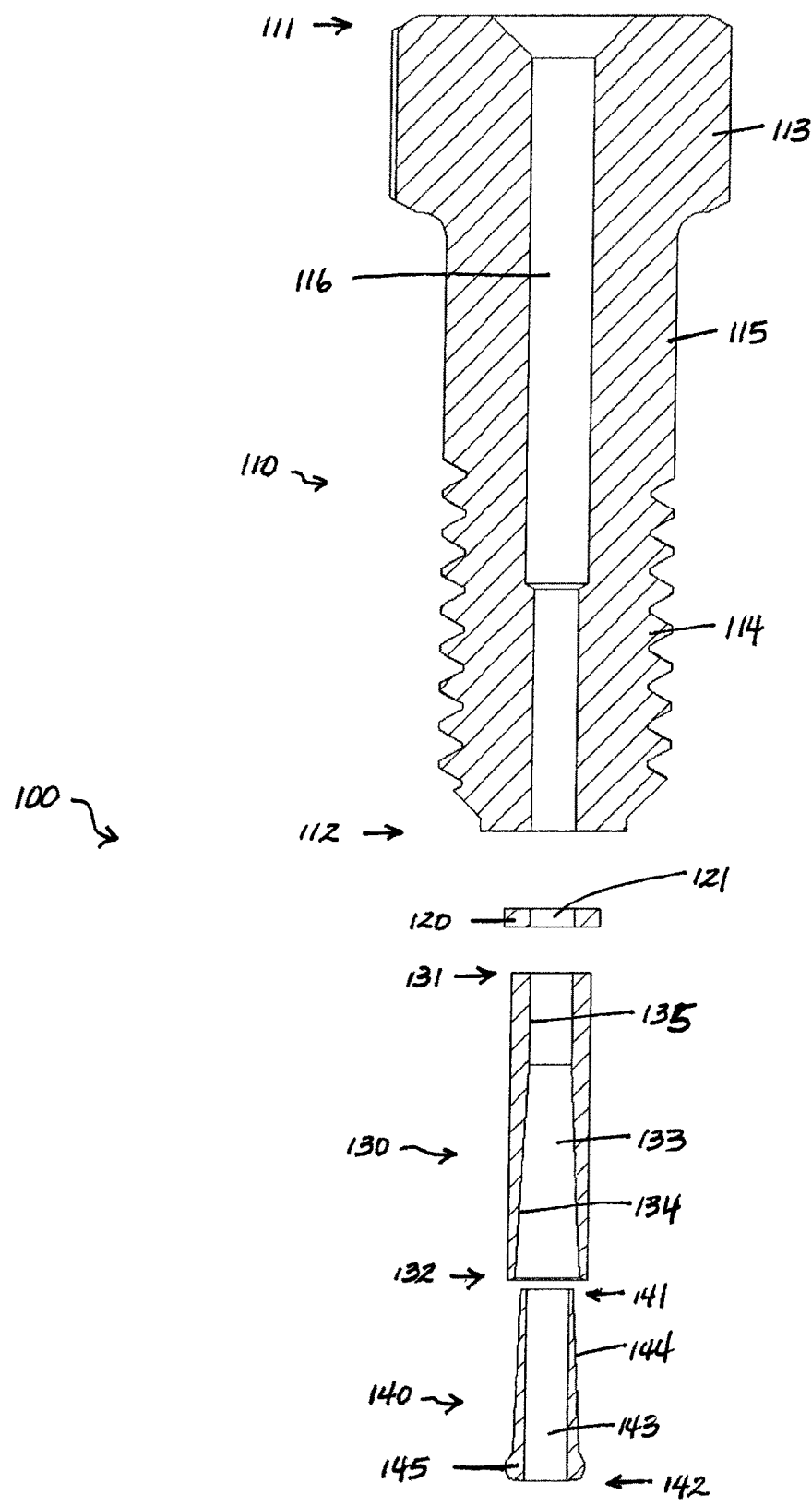
FIG. 2 is an exploded cross-sectional view of various components of an embodiment of a connection assembly in accordance with one aspect of the present disclosure.

Referring now to FIG. 2, a first embodiment of a connection assembly 100 is shown. As shown in FIG. 2, the connection assembly 100 includes a nut 110, an optional washer 120, a locktube 130 and a ferrule 140. Nut 110 comprises nut head 113, which is proximal to the first end 111 of the nut 110. An externally threaded portion 114 is proximal to the other or second end 112 of the nut 110. Nut 110 also comprises an externally non-threaded portion 115 between the nut head 113 and the externally threaded portion 114. Nut 110 also defines an internal passageway 116 that extends from the first end 111 to the second end 112 of the nut 110. Washer 120 defines an internal passageway 121. Locktube 130 comprises a first end 131, a second end 132, and defines an internal passageway 133 that extends from the first end 131 to the second end 132 of the locktube 130. Locktube 130 also comprises an internal tapered portion 134 and an internal non-tapered portion 135. The non-tapered portion 135 of locktube 130 is generally deformed (by crimping or dimpling or swaging or could be welded) onto a tube (not shown in FIG. 2). This can be performed prior to use, or when a connection using assembly 100 is made by an operator. This allows axial loads (such as may be due to hydraulic pressure on an unsupported end of an assembly) to be transferred through the assembly 100 and to the supported end. Without this attachment process, an assembly can fail at anywhere from about 12,000-16,000 psi. This attachment process can also apply to other embodiments disclosed herein (for example, see connection assembly 200 herein below).

Still referring to FIG. 2, the internal tapered portion 134 of the locktube 130 forms a truncated conical shape. Ferrule 140 comprises a first end 141 and a second end 142, and defines an internal passageway 143 that extends from the first end 141 to the second end 142 of the ferrule 140. Ferrule 140 also comprises an external tapered portion 144 and an optional protrusion 145 proximal the second end 142 of the ferrule 140. The external tapered portion 144 of the ferrule 140 forms a truncated conical shape. Washer 120 serves as a thrust bearing as well as transfers the compressive loads of the locktube 130 into the nut 110 when a connection with the assembly 100 is made. Without the larger surface area of the washer 120, the nut 110 could deform at higher torque values (approximately 2 in-lb). In alternative embodiments (not shown) the washer shape could be integrated into the locktube (such as machined into the locktube). The washer 120 can rotate, so it should likely reduce the torque otherwise transferred to the nut due to reduced friction from rotation of the washer. In alternative embodiments (not shown) multiple washers could be stacked or different washer materials could be used to transfer the loads as well as reduce the friction, which in turn reduces the required assembly torque (e.g., such as to stay at finger tight levels).

As shown in FIG. 2, the internal tapered portion 134 of the locktube 130 and the external tapered portion 144 of the ferrule 140 each define an angle from the axis of the locktube 130 and ferrule 140, respectively. However, those skilled in the art will appreciate that the internal tapered portion 134 of the locktube 130 and external tapered portion 144 of the ferrule 140 can define different angles if desired, and can define angles that are about equal to each other, or differ from each other, depending upon the particular application. In addition, although a single angle for each is shown in FIG. 2, each can have multiple or differing angles in different portions thereof.

As shown in FIG. 2, nut 110, the washer 120, the locktube 130 and the ferrule 140 are preferably generally circular and symmetric about a center axis. As detailed herein, the externally threaded portion 114 of the nut 110 is adapted to be removably secured to a corresponding threaded portion of a port, a union, a fitting, or a component of an LC or other analytical instrument (AI) system (not shown). Those skilled in the art will appreciate that the externally threaded portion 114 of the nut 110 may be adapted so that it can be removably engaged with any sized port, union, fitting, or component of an LC or other AI system (not shown). The use of external threads on one element, such as the nut 110, versus internal threads, is a matter of selection. Those skilled in the art will therefore appreciate that the nut 110 in an alternative embodiment could have internal threads (not shown) located near a second end which could be engaged with external threads (not shown) located near the first end of an alternative embodiment of a port, union, fitting, or component of an LC or AI system (not shown).

In general, it is believed that the externally threaded portion 114 of the nut 110 and the shape and size of the washer 120, the locktube 130 and the ferrule 140 should be such that assembled connection assembly 100 and tubing extending therethrough (not shown in FIG. 2) may be easily secured to a port, union, fitting, or component of a LC or AI system (not shown), and may also be easily removed therefrom, in either case by rotating the nut head 113 (and thereby connection assembly 100) relative to the port, union, fitting, or component of a LC or AI system (not shown).

Generally, the rotational force or torque applied to connect to the nut 110, washer 120, locktube 130 and ferrule 140, and tubing extending therethrough (not shown in FIG. 2) to a port, union, fitting, or component in an LC or AI system (not shown) accomplishes two major tasks. First, the force of the connection of the connection assembly 100 needs to be sufficient to provide a sealed and leak proof connection to the port, union, fitting, or component of a LC or AI system (not shown). In addition, the force of the connection of the connection assembly 100 needs to be sufficient so that the tubing (not shown in FIG. 2) is securely held and is sufficient to prevent detachment due to the hydraulic force of the fluid moving through the tubing (not shown in FIG. 2). It is believed that the latter function typically involves greater forces than the former. It is believed that the connection assembly 100 (such as shown in FIG. 2) provides an advantage in that it allows for better connections at higher pressures without requiring higher forces to connect connection assembly 100, and without substantial deformation of the tubing.

Figure 3:
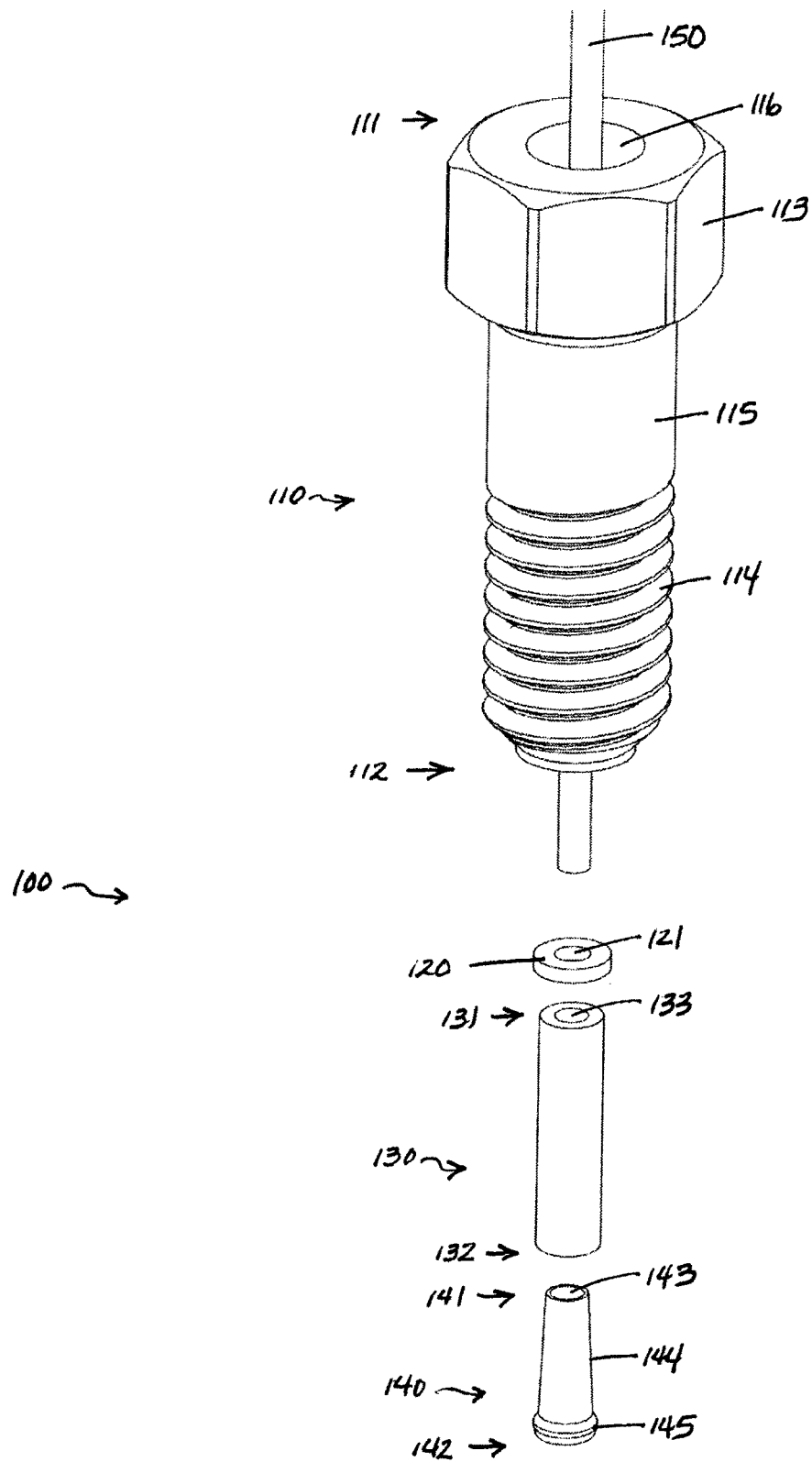
FIG. 3 is an exploded top perspective side view of the connection assembly of FIG. 2 with a tube shown through the nut.

FIG. 3 shows an exploded top perspective side view of the connection assembly 100 of FIG. 2 with a tube 150 shown extending through the nut 110. Like features and elements in the drawings have the same numerals in the various figures. Once again the connection assembly 100 includes a nut 110, a washer 120, a locktube 130 and a ferrule 140. Nut 110 comprises nut head 113, which as shown in FIG. 3 is hexagonal and proximal to the first end 111 of the nut 110. Although not shown, in other embodiments the nut head can be generally circular with a plurality of splines. Those skilled in the art will realize that the outer diameter of nut head 113 may have other shapes, including non-circular shapes, if desired, such as having flat or concave surface portions, to allow an operator to more easily grip and rotate nut 110. Nut 110 again comprises an externally threaded portion 114 proximal to the second end 112 of the nut 110, and an externally non-threaded portion 115 between the nut head 113 and the externally threaded portion 114. Tube 150 extends through internal passageway 116 of the nut 110. Visible in FIG. 3 are washer 120, which defines an internal passageway 121, locktube 130, which comprises a first end 131, a second end 132, and defines an internal passageway 133 that extends from the first end 131 to the second end 132 of the locktube 130, and ferrule 140, which comprises a first end 141 and a second end 142, and defines an internal passageway 143 that extends from the first end 141 to the second end 142 of the ferrule 140, external tapered portion 144 and an optional protrusion 145 proximal the second end 142 of the ferrule 140.

Figure 4:
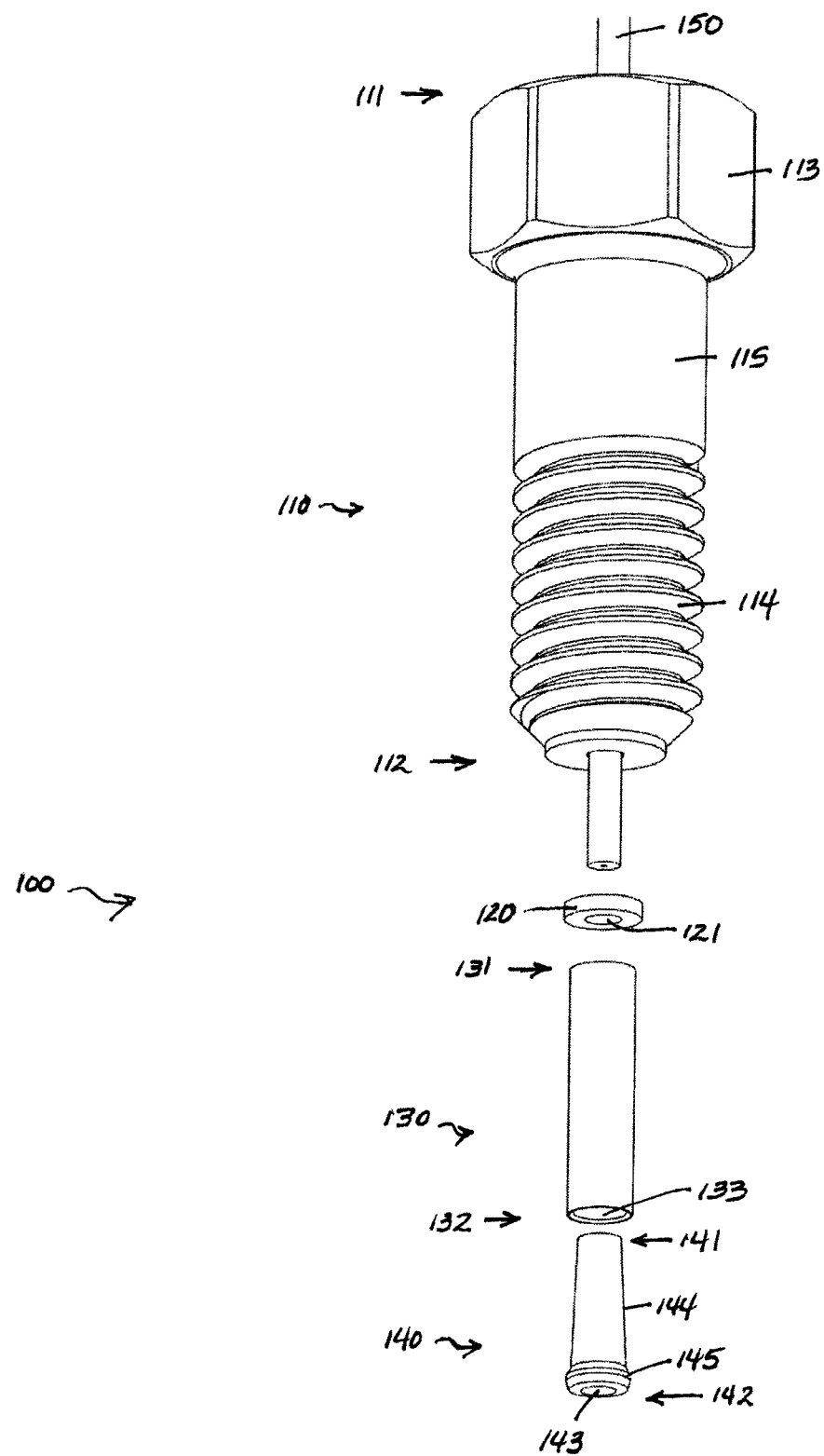
FIG. 4 is an exploded bottom perspective side view of the connection assembly of FIG. 2 with a tube shown through the nut.

FIG. 4 shows an exploded bottom perspective side view of the connection assembly 100 of FIG. 2 with a tube 150 shown extending through the nut 110. Once again the connection assembly 100 includes a nut 110, a washer 120, a locktube 130 and a ferrule 140. Nut 110 comprises nut head 113, which as shown in FIG. 4 is hexagonal and proximal to the first end 111 of the nut 110. Nut 110 again comprises an externally threaded portion 114 proximal to the second end 112 of the nut 110, and an externally non-threaded portion 115 between the nut head 113 and the externally threaded portion 114. Tube 150 extends through internal passageway (not visible in FIG. 4) of the nut 110. Visible in FIG. 4 are washer 120, which defines an internal passageway 121, locktube 130, which comprises a first end 131, a second end 132, and defines an internal passageway 133 that extends from the first end 131 to the second end 132 of the locktube 130, and ferrule 140, which comprises a first end 141 and a second end 142, and defines an internal passageway 143 that extends from the first end 141 to the second end 142 of the ferrule 140, external tapered portion 144 and an optional protrusion 145 proximal the second end 142 of the ferrule 140.

Figure 5:
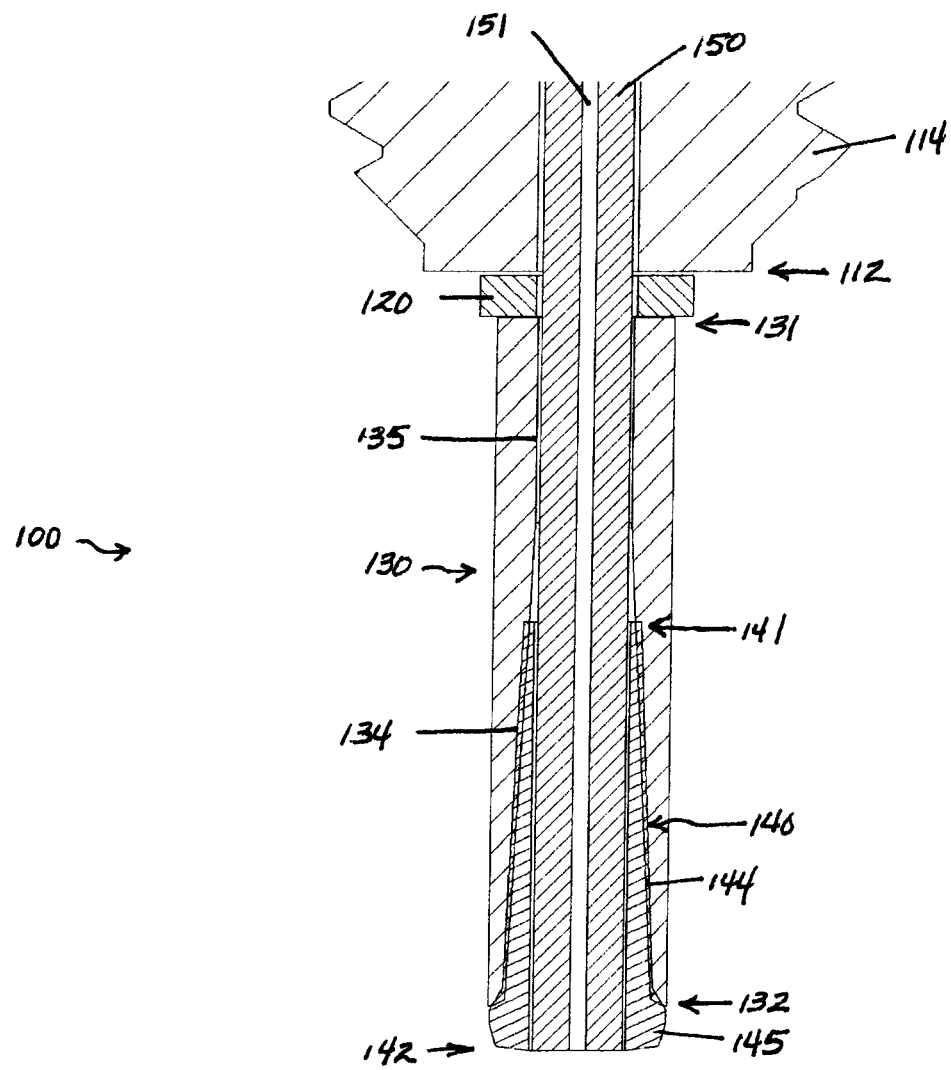
FIG. 5 is a cross-sectional view of the bottom portion of the tube connection assembly of FIG. 3 and FIG. 4 when assembled.

FIG. 5 shows a cross-section of the bottom portion of the connection assembly 100 and tube 150 shown in FIG. 3 and FIG. 4 upon assembly. Shown in FIG. 5 is the bottom portion of the externally threaded portion 114 and second end 112 of nut 110, washer 120, locktube 130 having first end 131, second end 132, internally tapered portion 134 and internally non-tapered portion 135, ferrule 140 having first end 141, second end 142, externally tapered portion 144 and optional protrusion 145, and tube 150 comprising internal passageway 151 extending through the nut 110, washer 120, locktube 130 and ferrule 140. As shown in FIG. 5, the internally tapered portion 134 of the locktube 130 is adapted to receive and securely hold the externally tapered portion 144 of the ferrule 140, and the optional protrusion 145 of the ferrule 140 abuts the second end 132 of the locktube 130, when the connection assembly 100 is assembled. As shown in FIG. 5 the internally tapered portion 134 of the locktube 130 and the externally tapered portion 144 of the ferrule 140 include a very shallow taper, which is believed to generally enable high mechanical advantage at relatively low nut torque (for example about 2 in-lb). This generally also becomes a locking taper, resulting in the locktube and ferrule remaining together when removed from a port, union, fitting, or component of a LC or AI system (not shown). Additionally, as shown in FIG. 5 the externally tapered portion 144 of the ferrule 140 is relatively thin, so as to maximize compression between the ferrule 140 and the tube 150 upon assembly.

Figure 6:
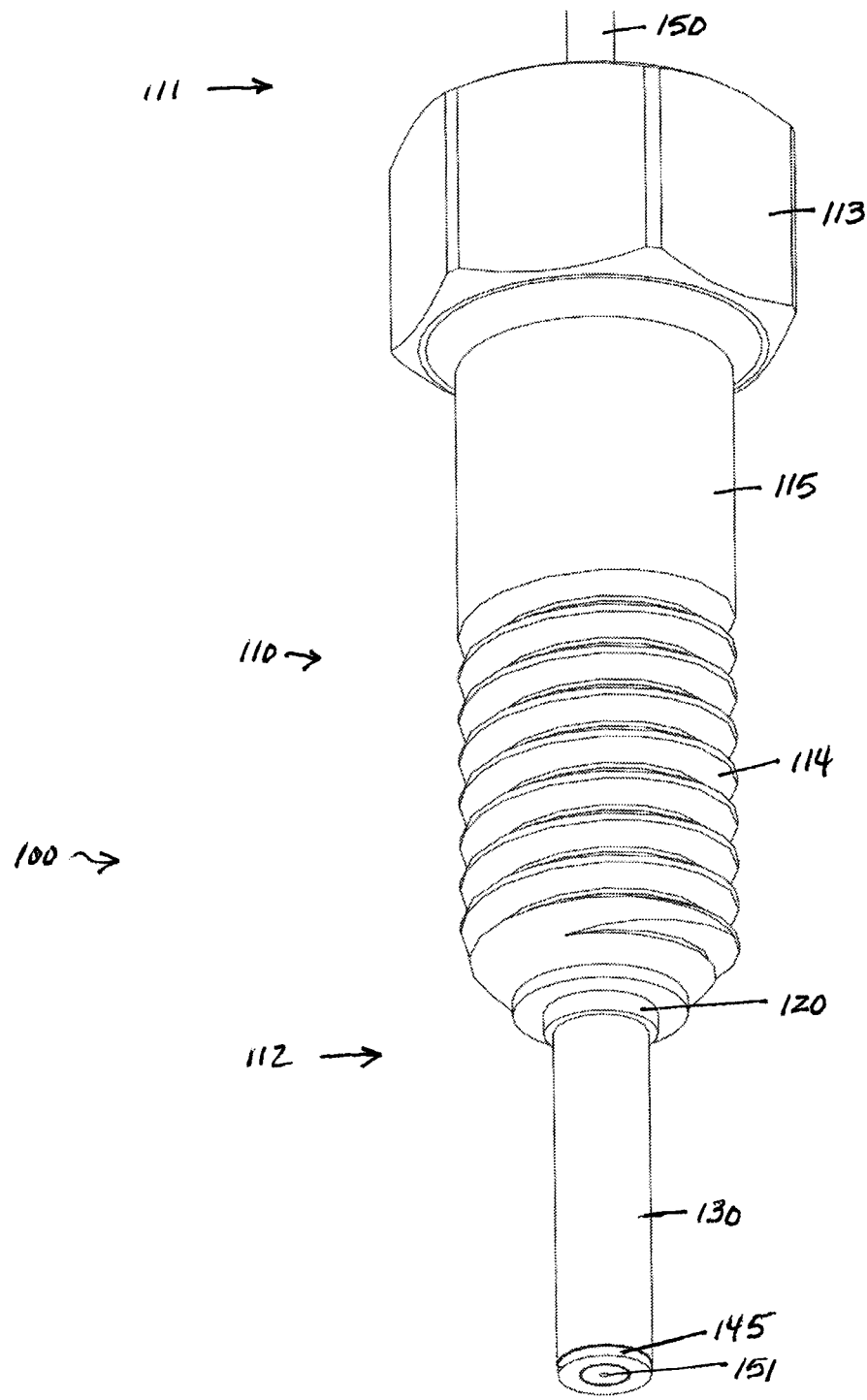
FIG. 6 is a bottom perspective side view of the tube connection assembly of FIG. 3 and FIG. 4 when assembled.

FIG. 6 shows a bottom perspective side view of the connection assembly 100 and tube 150 of FIG. 4 upon assembly. Visible in FIG. 6 is nut 110, washer 120, locktube 130 and optional protrusion 145 of ferrule 140 (not completely visible in FIG. 6). Nut 110 comprises nut head 113, which as shown in FIG. 6 is hexagonal and proximal to the first end 111 of the nut 110. Nut 110 again comprises an externally threaded portion 114 proximal to the second end 112 of the nut 110, and an externally non-threaded portion 115 between the nut head 113 and the externally threaded portion 114. Tube 150 comprising internal passageway 151 extends through internal passageway (not visible in FIG. 4) of the nut 110, washer 120, locktube 130 and ferrule 140 (not completely visible in FIG. 6).

Figure 7:
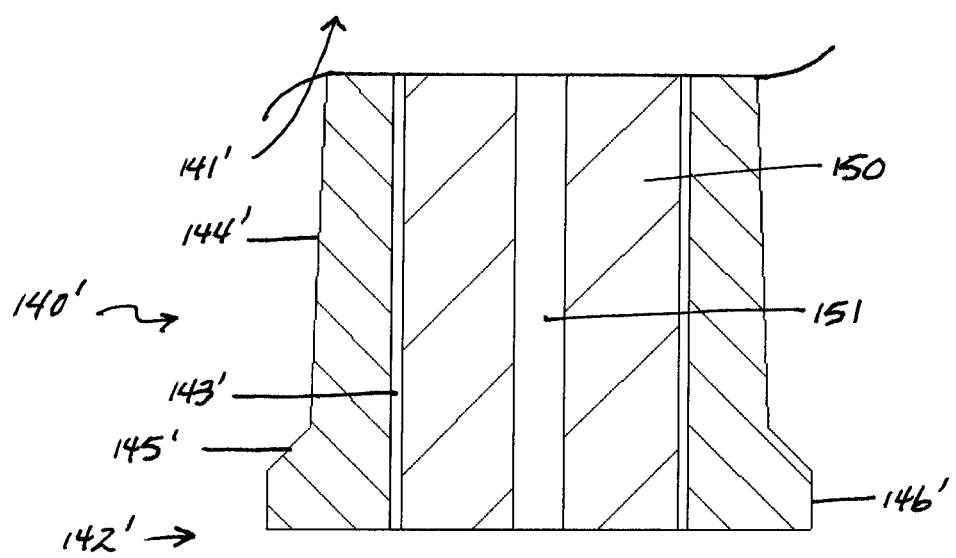
FIG. 7 is a cross-sectional view of the bottom portion of an alternative ferrule for use with the connection assembly of FIG. 2.

FIG. 7 shows a cross-sectional view of the bottom portion of an alternative ferrule 140' for use with the nut 110, washer 120 and locktube 130. Alternative ferrule 140' comprises a first end 141' (not shown in FIG. 7) and a second end 142', and defines an internal passageway 143' that extends from the first end 141' to the second end 142' of the alternative ferrule 140'. Alternative ferrule 140' also comprises a first external tapered portion 144', a second external tapered portion 145', and an external non-tapered portion 146' proximal the second end 142' of the alternative ferrule 140'. The first external tapered portion 144' and second external tapered portion 145' of the alternative ferrule 140' each form a truncated conical shape. Also shown in FIG. 7 is tube 150 comprising internal passageway 151 extending through internal passageway 143' of the ferrule 140'.

Figure 8:
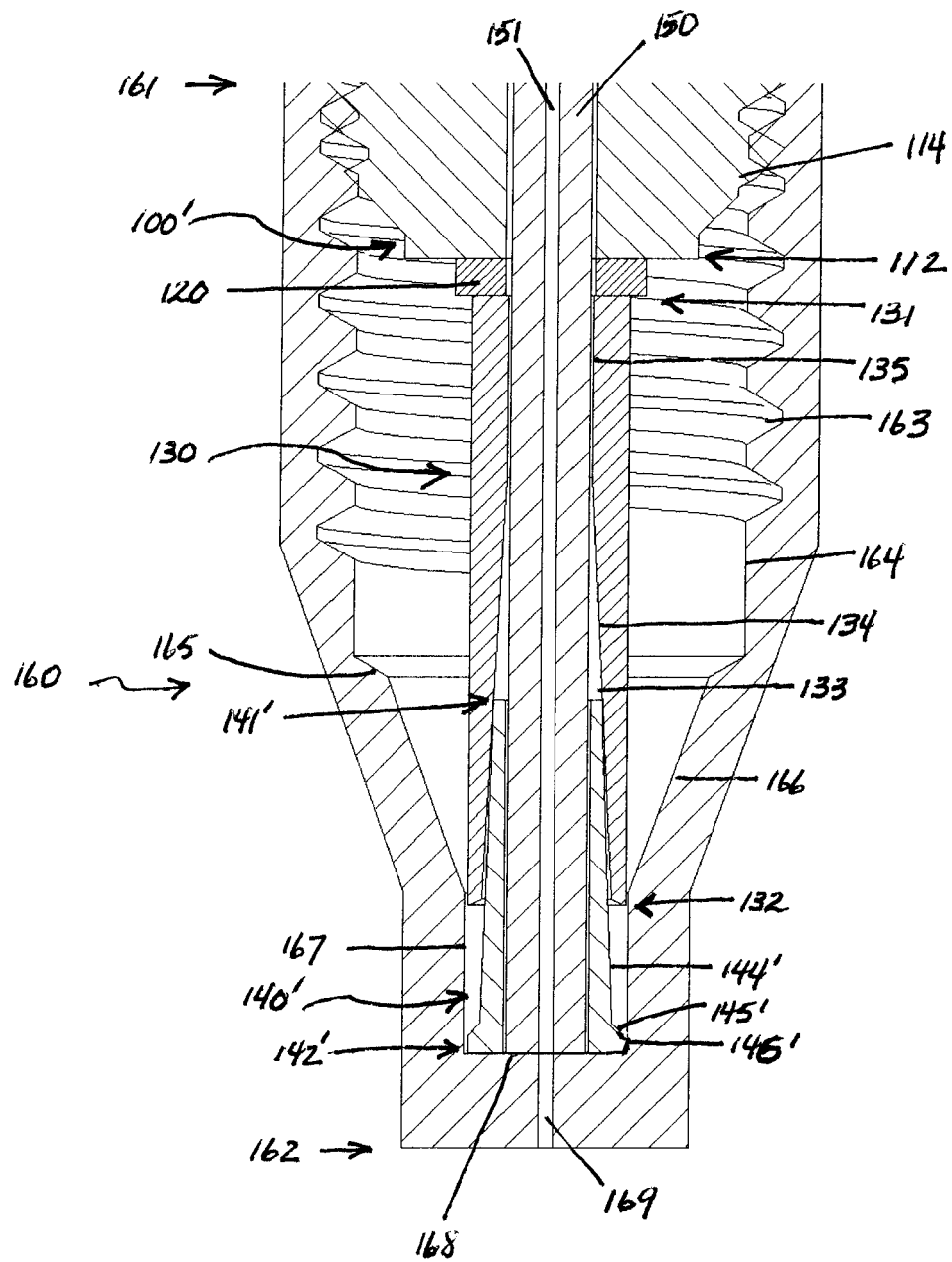
FIG. 8 is a cross-sectional view of the bottom portion of a tube connection assembly similar to that shown in FIG. 5 with alternative ferrule shown in FIG. 7 upon initial engagement with a port.

FIG. 8 shows a cross-sectional view of the bottom portion of alternative connection assembly 100' and tube 150 (similar to that shown in FIG. 3 and FIG. 4 except with alternative ferrule 140' shown in FIG. 7) upon initial engagement in port 160. Shown in FIG. 8 is the bottom portion of the externally threaded portion 114 and second end 112 of nut 110, washer 120, locktube 130 having first end 131, second end 132, internal passageway 133, internally tapered portion 134 and internally non-tapered portion 135, alternative ferrule 140' having first end 141', second end 142', first externally tapered portion 144', second externally tapered portion 145' and externally non-tapered portion 146', and tube 150 comprising internal passageway 151 extending through the nut 110, washer 120, locktube 130 and ferrule 140. Port 160 comprises first end 161, second end 162, internally threaded portion 163, first internally non-tapered portion 164, first internally tapered portion 165, second internally tapered portion 166, second internally non-tapered portion 167, face 168 and internal passageway 169. As shown in FIG. 8, as connection assembly 100' and tube 150 is initially engaged with port 160, the first externally tapered portion 144' of the ferrule 140 is forced into the internally tapered portion 134 of the locktube 130.

Figure 9:
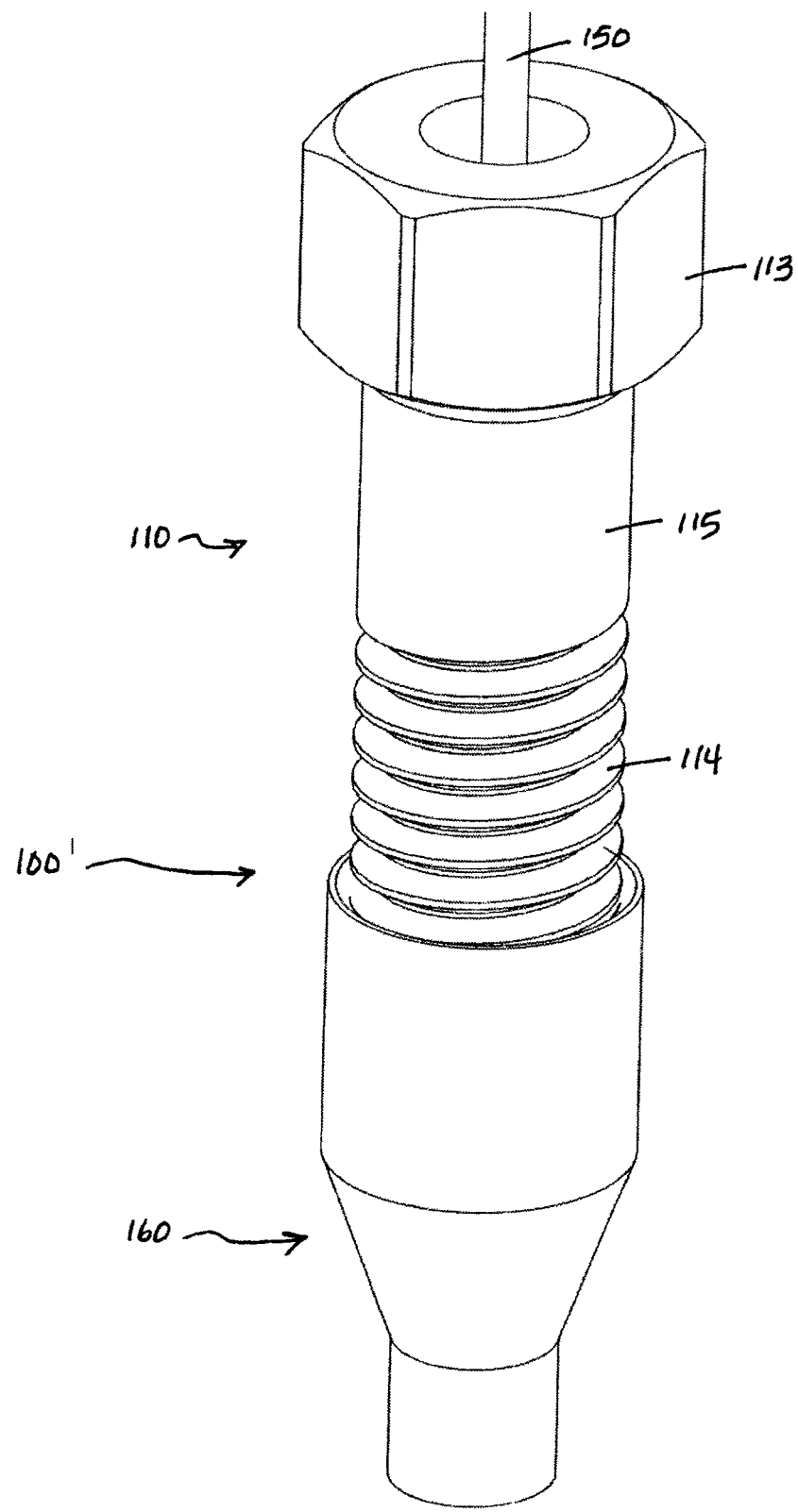
FIG. 9 is a top perspective side view of the tube connection assembly of FIG. 8 engaged in a port.

FIG. 9 shows a top perspective side view of the connection assembly 100' and tube 150 upon engagement with port 160. The only portion of the connection assembly 100' visible in FIG. 9 is the nut 110, comprising nut head 113, externally threaded portion 114 and externally non-threaded portion 115.

Figure 10:
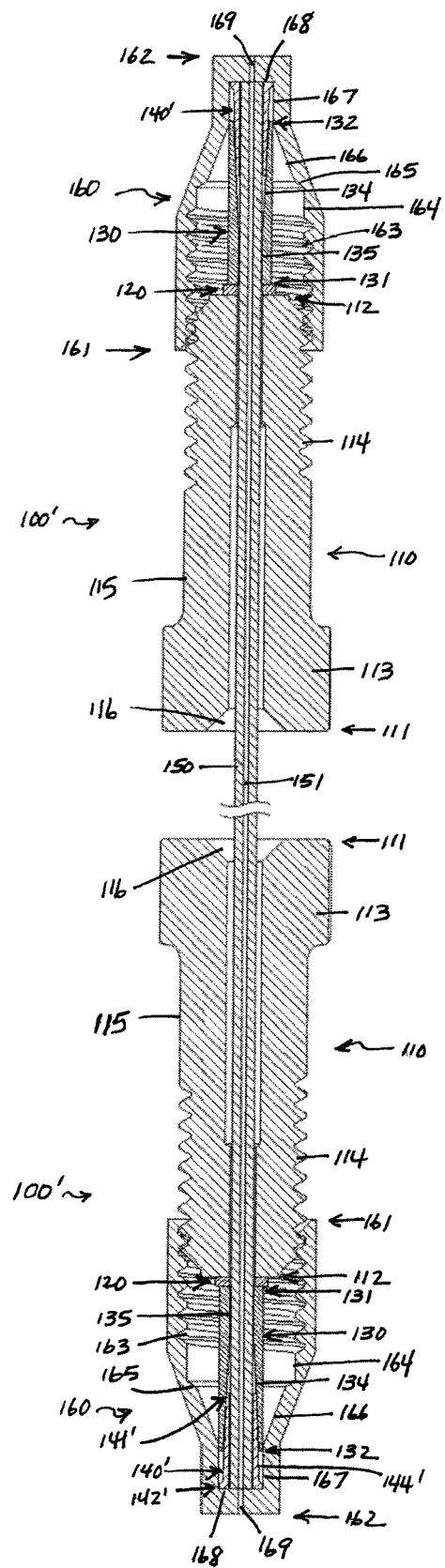
FIG. 10 is a cross-sectional view of the tube connection assembly of FIG. 8 upon initial engagement with a port with a second connection assembly at the other end of the tube upon initial engagement with a port.

FIG. 10 is a cross-sectional view of the tube connection assembly 100' as shown in FIG. 8 upon complete engagement with a port with a second tube connection assembly 100' as shown in FIG. 8 upon complete engagement with a second port at the other end of the tube. Each connection assembly 100' in FIG. 10 includes a nut 110, a washer 120, a locktube 130 and alternative ferrule 140'. Nut 110 comprises nut head 113, which as shown in FIG. 10 is hexagonal and proximal to the first end 111 of the nut 110. Although not shown, in other embodiments the nut head can be generally circular with a plurality of splines. Those skilled in the art will realize that the outer diameter of nut head 113 may have other shapes, including non-circular shapes, if desired, such as having flat or concave surface portions, to allow an operator to more easily grip and rotate nut 110. Nut 110 again comprises an externally threaded portion 114 proximal to the second end 112 of the nut 110, and an externally non-threaded portion 115 between the nut head 113 and the externally threaded portion 114. Tube 150 extends through internal passageway 116 of the nut 110. Each connection assembly 100' also includes washer 120, which defines an internal passageway 121 (not visible in FIG. 10), locktube 130, which comprises a first end 131, a second end 132, and defines an internal passageway (not visible in FIG. 10) that extends from the first end 131 to the second end 132 of the locktube 130, and alternative ferrule 140', which comprises a first end 141' and a second end 142', and defines an internal passageway (not visible in FIG. 10) that extends from the first end 141' to the second end 142' of the alternative ferrule 140', first external tapered portion 144', second external tapered portion (not visible in FIG. 10) and external non-tapered portion 146' (not visible in FIG. 10) proximal the second end 142' of the alternative ferrule 140'. Each of ports 160 comprise first end 161, second end 162, internally threaded portion 163, first internally non-tapered portion 164, first internally tapered portion 165, second internally tapered portion 166, second internally non-tapered portion 167, face 168 and internal passageway 169. As shown in FIG. 10, as each of connection assembly 100' and tube 150 is engaged with each corresponding port 160, the first externally tapered portion 144' of the ferrule 140 is forced into the internally tapered portion 134 of the locktube 130.

It will be appreciated that the nut 110, washer 120, locktube 130 and ferrule 140 in connection assembly 100, as well as alternative ferrule 140' in connection assembly 100', can comprise a number of different materials. Nut 110, washer 120, locktube 130 and ferrule 140 can comprise a metal, such as stainless steel, or can comprise a polymer, such as a polyaryletherketone (PAEK), including, but not limited to, polyetherketone (PEK), polyetheretherketone (PEEK™), polyetherketoneketone (PEKK), polyetheretherketoneketone (PEEKK), and polyetherketoneetherketoneketone (PEKEKK). In addition, each of the components of the connection assembly 100 or connection assembly 100' can comprise the same material, or some or all of the components can comprise different materials. It will be appreciated that a variety of metals and polymers may be selected for the components of the connection assembly 100 or connection assembly 100' depending on the particular application, as that may involve a particular type of sample, a particular type of solvent, and/or a particular pressure range. In addition, the selection of materials for the tube 150, such as PEEK™ or other polymers, and metal, including, but not limited to, stainless steel, titanium, nickel or gold, may lead to a selection of a particular material for the components of the connection assembly 100 or connection assembly 100'. In addition, PEEK™ (or other polymers) may be used that is reinforced with carbon, carbon fibers, glass fibers, or steel fibers, or the like. Other polymer materials which may be used include, but are not limited to, TEFLON®, TEFZEL®, DELRIN®, polyphenylene sulfide (PPS), polypropylene, and others, depending on the foregoing factors and perhaps others, such as cost. Those skilled in the art will further appreciate that connection assembly 100 and connection assembly 100' are shown for connecting tube 150 to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

Those skilled in the art will appreciate that the externally threaded portion 114 of the nut 110 may be adapted so that it can be removably engaged with any sized port, union, fitting, or component of an LC or other AI system (not shown). The use of external threads on one element, such as the nut 110, versus internal threads, is a matter of selection. Those skilled in the art will therefore appreciate that the nut 110 in an alternative embodiment could have internal threads (not shown) located near a second end which could be engaged with external threads (not shown) located near the first end of an alternative embodiment of a port, union, fitting, or component of an LC or AI system (not shown).

In certain applications utilizing PEEK™, the PEEK™ used in fabrication of the nut 110, washer 120, locktube 130, ferrule 140, and/or tube 150 may be annealed according to manufacturer's recommendations. In general, the PEEK™ is ramped from about 70° F. to between about 300° F. and about 320° F. over about 40 to about 60 minutes, held at about 300° F. to about 320° F. for about 150 to about 180 minutes, ramped from between about 300° F. and about 320° F. to between about 392° F. and about 560° F. over about 90 minutes to about 300 minutes, held between about 392° F. and about 560° F. for between about 240 minutes and about 2880 minutes, and ramped down to between about 70° F. and about 284° F. over about 360 minutes to about 600 minutes. However, the skilled artisan will readily understand that different annealing protocols may be used in other applications.

In order for a connection assembly 100 to seal, it should generally remain in compression (relative to the bottom of the port) throughout all environmental conditions. Therefore, in certain aspects a coating with a high coefficient of friction is applied to at least a portion of the internal bore surface of the described connection assembly 100 or 100'. The high coefficient of friction between the outer surface of the tube 150 and the internal bore surface of the connection assembly 100 or 100' keeps the tube from extruding out of the port during pressurization, which results in dramatically increased burst pressure. In such embodiments the fitting connection or assembly is coated at the internal bore surface that contacts the tube starting at approximately 0.005 inches, about 0.0075 inches, about 0.01 inches, or about 0.02 inches from either or both ends of the connection assembly 100 or 100'. Coatings suitable for use with the presently described fitting connection or assembly include, but are not limited to, nickel, silica carbide, copper, and diamond coatings, and combinations thereof.

Methods of using the connection assemblies 100 and 100' are now described in further detail. For convenience, the following discussion uses assembly 100 as an example, but those skilled in the art will understand that this also applies to other embodiments, such as assembly 100'. An operator can engage the externally threaded portion 114 of the nut 110 with the internally threaded portion 163 of a port 160, or fitting, union or other component of a LC or AI system (not shown). Once the externally threaded portion 114 of the nut 110 and the internally threaded portion 163 of a port 160, or fitting, union, or other component of a LC or AI system (not shown) begin to mate or engage, the operator then rotates the nut head 113 of the connection assembly 100 relative to the port 160, or fitting, union or other component of a LC or AI system (not shown), rotates the port 160, or fitting, union or other component of a LC or AI system (not shown) relative to the nut head 113 of the connection assembly 100, or rotates both the nut head 113 of the connection assembly 100 and the port 160, or fitting, union or other component of a LC or AI system (not shown) relative to each other, to the desired torque (in general finger-tight, or about 2 in-lb). By so rotating the nut head 113 of the connection assembly 100 and the port 160, or fitting, union or other component of a LC or AI system (not shown) relative to one another, the operator drives the ferrule 140 further into the internally tapered portion 134 of the locktube 130. In doing so, the operator thus forces the externally tapered portion 144 of the ferrule 140 against the internally tapered portion 134 of the locktube 130, thus engaging the ferrule 140 with the locktube 130. In doing so, the external tapered portion 144 of the ferrule 140 is compressed and held firmly against the internally tapered portion 134 of the locktube 130, thereby forming a leak-proof connection. Because the external tapered portion 144 of the ferrule 140 may be deformed or compressed as it is forced against the internal tapered portion 134 of the locktube 130, a leak-proof connection may be obtained by the operator without the use of additional tools such as a wrench, pliers or the like, although tools, such as a torque wrench, may be used in certain applications. In certain embodiments the ferrule 130 is pre-swaged with the locktube 140, which secures the ferrule 130 to the locktube 140. Additionally, the locktube 140 could then be crimped to the fluidic tube 150, which locks the locktube 140 to the fluidic tube 150 and could allow the assembly 100 to perform at higher fluid pressures without failing.

To disconnect a connection assembly 100, an operator may either rotate the connection assembly 100 relative to the port 160, or fitting, union or other component of a LC or AI system (not shown), rotate the port 160, or fitting, union or other component of a LC or AI system (not shown) relative to the connection assembly 100, or rotate both the port 100, or fitting, union or other component of a LC or AI system (not shown) and the connection assembly 100 relative to each other. By rotating the port 160, or fitting, union or other component of a LC or AI system (not shown) and/or the connection assembly 100 relative to one another, the operator thus rotates the externally threaded portion 114 of nut 110 and the internally threaded portion 163 of the port 160, or fitting, union or other component of a LC or AI system (not shown), respectively, and thereby disengages the connection between such threaded portions. At this point, the operator can reuse the connection assembly 100 and the leak-proof connection it provides. By selecting the direction of the threading of the externally threaded portion 114 of the nut 110 and internally threaded portion 163 of the port 160, or fitting, union or other component of a LC or AI system (not shown), respectively, the operator can turn the entire connection assembly 100 (when connected) by turning or rotating nut 110, such that the connection assembly 100 rotates relative to the port 160, or fitting, union or other component of a LC or AI system (not shown) and disengages therefrom. Thus, the entire connection assembly 100 is easily disconnected from the port 160, or fitting, union or other component of a LC or AI system (not shown).

Figure 11:
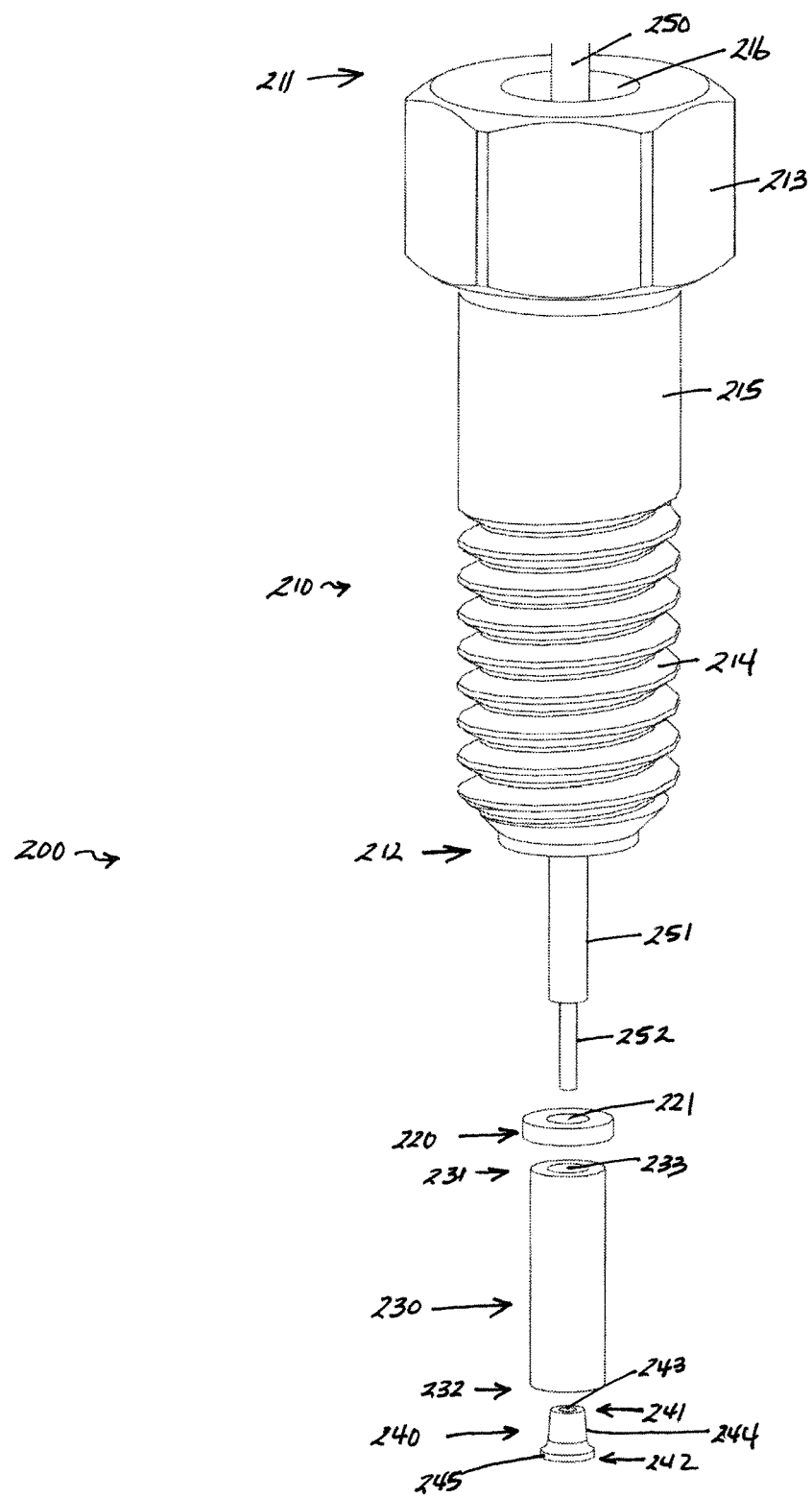
FIG. 11 is an exploded top perspective side view of various components of an alternate embodiment of a tube connection assembly in accordance with another aspect of the present disclosure.

Referring now to FIG. 11, an exploded top perspective side view of an alternate embodiment of an assembly 200 is shown. As shown in FIG. 11, the assembly 200 includes a nut 210, an optional washer 220, locktube 230, ferrule 240 and tube 250. Nut 210 comprises first end 211 and second end 212, nut head 213, which is proximal to the first end 211 of the nut 210, an externally threaded portion 214 proximal to the other or second end 212 of the nut 210, externally non-threaded portion 215 between the nut head 213 and the externally threaded portion 214 and internal passageway 216 through the nut 210 from the first end 211 to the second end 212 of the nut 210. Washer 220 defines an internal passageway 221. Locktube 230 comprises a first end 231, a second end 232, and defines an internal passageway 233 that extends from the first end 231 to the second end 232 of the locktube 230. Ferrule 240 comprises a first end 241 and a second end 242, and defines an internal passageway 243 that extends from the first end 241 to the second end 242 of the ferrule 240. Ferrule 240 also comprises an external tapered portion 244 and an optional protrusion 245 proximal the second end 242 of the ferrule 240. The external tapered portion 244 of the ferrule 240 forms a truncated conical shape. Tube 250 comprises a strain relief tube 251 and an inner tube 252.

Figure 12:
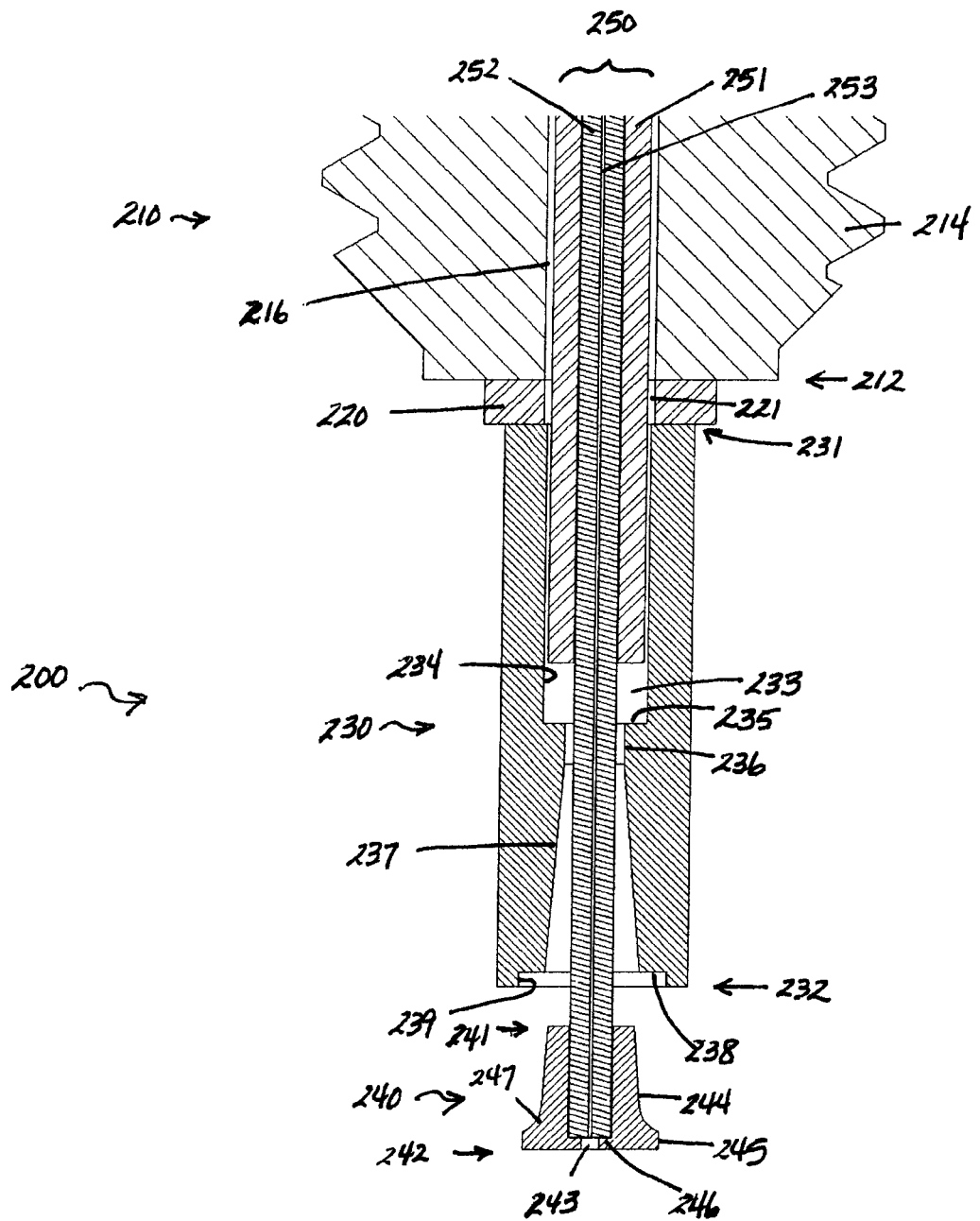
FIG. 12 is a cross-sectional view of the bottom portion of the tube connection assembly of FIG. 11 when assembled.

Additional features of the assembly 200 are shown in FIG. 12, which is a cross-sectional view of the lower portion of the assembly 200 shown in FIG. 11 upon partial assembly. Like features and elements in the drawings have the same numerals in the various figures. Nut 210 has a first end (not shown in FIG. 12), a second end 212, a nut head (not shown in FIG. 12), an externally non-threaded portion (not shown in FIG. 12), an externally threaded portion 214, and internal passageway 216 that extends through nut 210. Washer 220 defines internal passageway 221. Locktube 230 comprises a first end 231 and a second end 232, an internal passageway 233 that extends from the first end 231 to the second end 232 of the locktube 230, a first internal non-tapered portion 234, a first internal lip 235, a second internal non-tapered portion 236, an internal tapered portion 237, a second internal lip 238, and a third internal non-tapered portion 239. Ferrule 240 comprises a first end 241, a second end 242, an internal passageway 243 that extends from the first end 241 to the second end 242 of the ferrule 240, an externally tapered portion 244, an optional external protrusion 245, an internal lip 246 and an external radius 247. The internally tapered portion 237 of the locktube is adapted to receive and securely hold the externally tapered portion 244 of the ferrule 240 when the assembly 200 is assembled. The externally threaded portion 214 of the nut 210 is adapted to be removably secured to a corresponding threaded portion of a port, a fitting, a union, or a component of an LC or other analytical instrument (AI) system (not shown).

Figure 13:
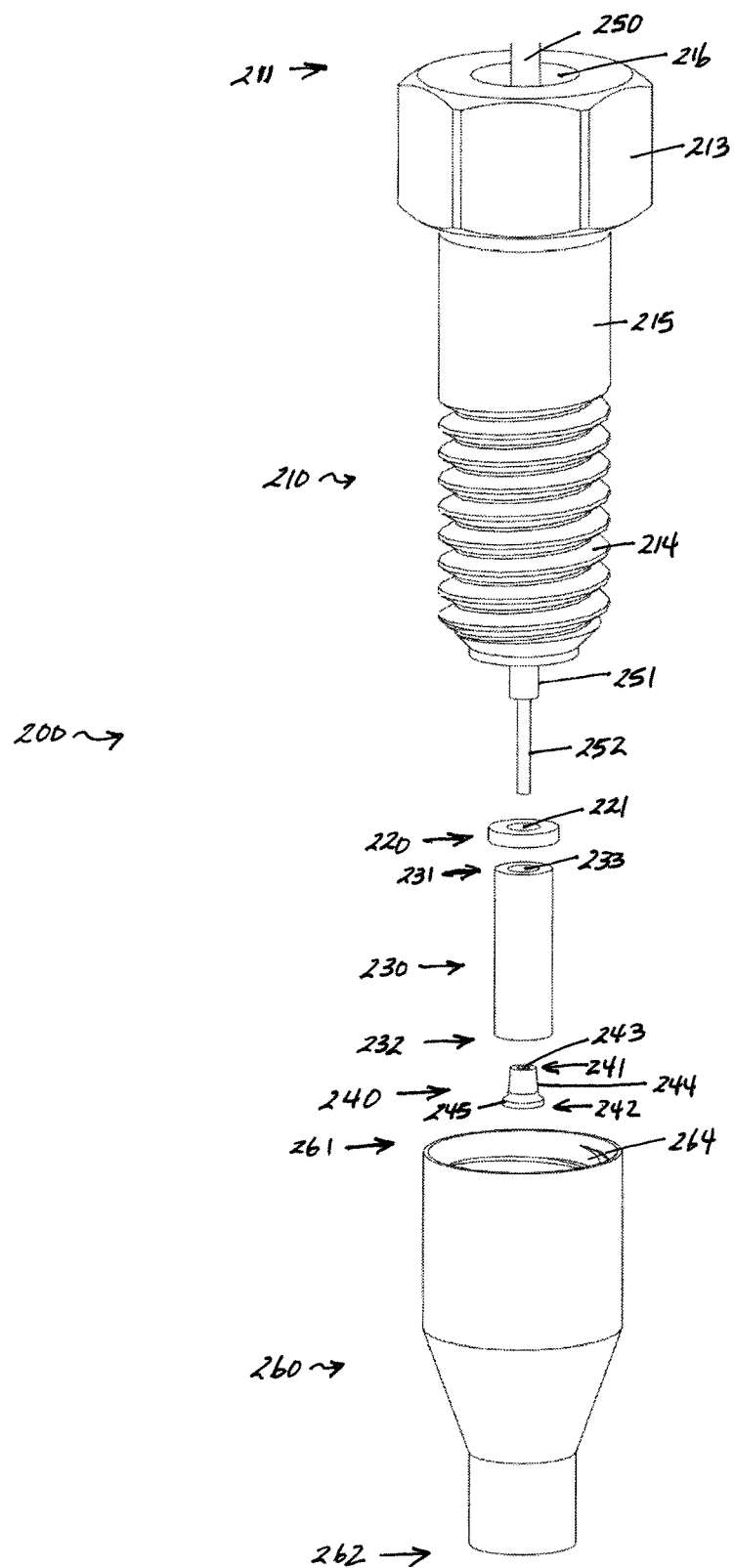
FIG. 13 is an exploded top perspective side view of the tube connection assembly of FIG. 11 and a port.

Referring now to FIG. 13, an exploded top perspective side view of an alternate embodiment of assembly 200 and port 260 is shown. As shown in FIG. 13, the assembly 200 includes a nut 210, washer 220, locktube 230, ferrule 240 and tube 250. Nut 210 comprises first end 211 and second end 212, nut head 213, which is proximal to the first end 211 of the nut 210, an externally threaded portion 214 proximal to the other or second end 212 of the nut 210, externally non-threaded portion 215 between the nut head 213 and the externally threaded portion 214 and internal passageway 216 through the nut 210 from the first end 211 to the second end 212 of the nut 210. Washer 220 defines a passageway 221.

Locktube 230 comprises a first end 231, a second end 232, and defines an internal passageway 233 that extends from the first end 231 to the second end 232 of the locktube 230. Ferrule 240 comprises a first end 241 and a second end 242, and defines an internal passageway 243 that extends from the first end 241 to the second end 242 of the ferrule 240. Ferrule 240 also comprises an external tapered portion 244 and an optional protrusion 245 proximal the second end 242 of the ferrule 240. The external tapered portion 244 of the ferrule 240 forms a truncated conical shape. Tube 250 comprises a strain relief tube 251 and an inner tube 252. Port 260 comprises a first end 261, a second end 262 and an internally threaded portion 264.

Figure 14:
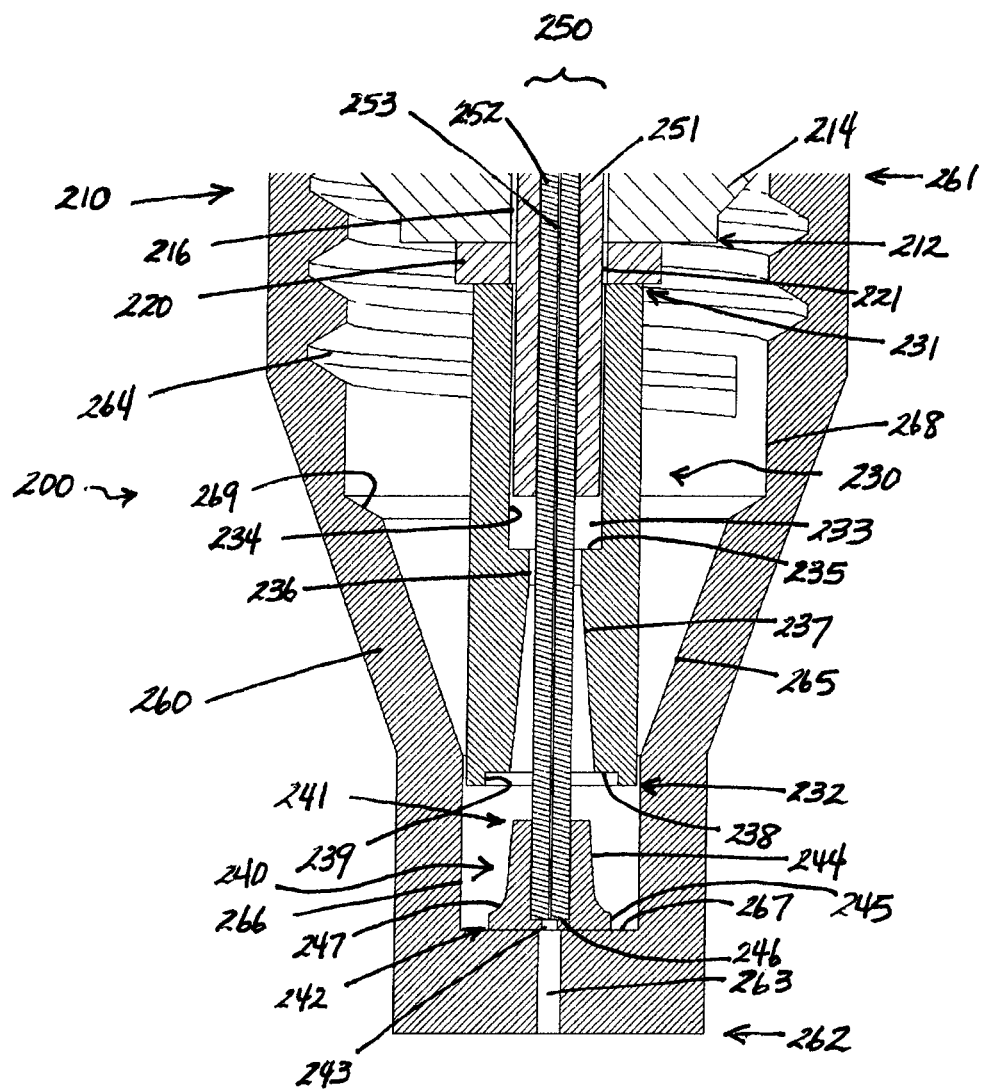
FIG. 14 is cross-sectional view of the bottom portion of the tube connection assembly of FIG. 11 upon initial engagement with the port.

FIG. 14 is a cross-sectional view of the lower portion of the assembly 200 shown in FIG. 11 upon initial engagement with port 260. Nut 210 has a first end (not shown in FIG. 14), a second end 212, a nut head (not shown in FIG. 14), an externally non-threaded portion (not shown in FIG. 14), an externally threaded portion 214, and internal passageway 216 that extends through nut 210. Washer 220 defines internal passageway 221. Locktube 230 comprises a first end 231 and a second end 232, an internal passageway 233 that extends from the first end 231 to the second end 232 of the locktube 230, a first internal non-tapered portion 234, a first internal lip 235, a second internal non-tapered portion 236, an internal tapered portion 237, a second internal lip 238, and a third internal non-tapered portion 239. Ferrule 240 comprises a first end 241, a second end 242, an internal passageway 243 that extends from the first end 241 to the second end 242 of the ferrule 240, an externally tapered portion 244, an optional external protrusion 245, an internal lip 246 and an external radius 247. The internally tapered portion 237 of the locktube is adapted to receive and securely hold the externally tapered portion 244 of the ferrule 240 when the assembly 200 is assembled. Port 260 comprises a first end 261, second end 262, an internal passageway 263 that extends from the first end 261 to the second end 262 of the port 260, internally threaded portion 264, internal non-threaded portion 268, first internal tapered portion 269, second internal tapered portion 265, first internal non-tapered portion 266 and face 267. The externally threaded portion 214 of the nut 210 is adapted to be removably secured to the corresponding internally threaded portion 264 of the port 260, or a fitting, a union, or other component of an LC or other analytical instrument (AI) system (not shown).

Figure 15:
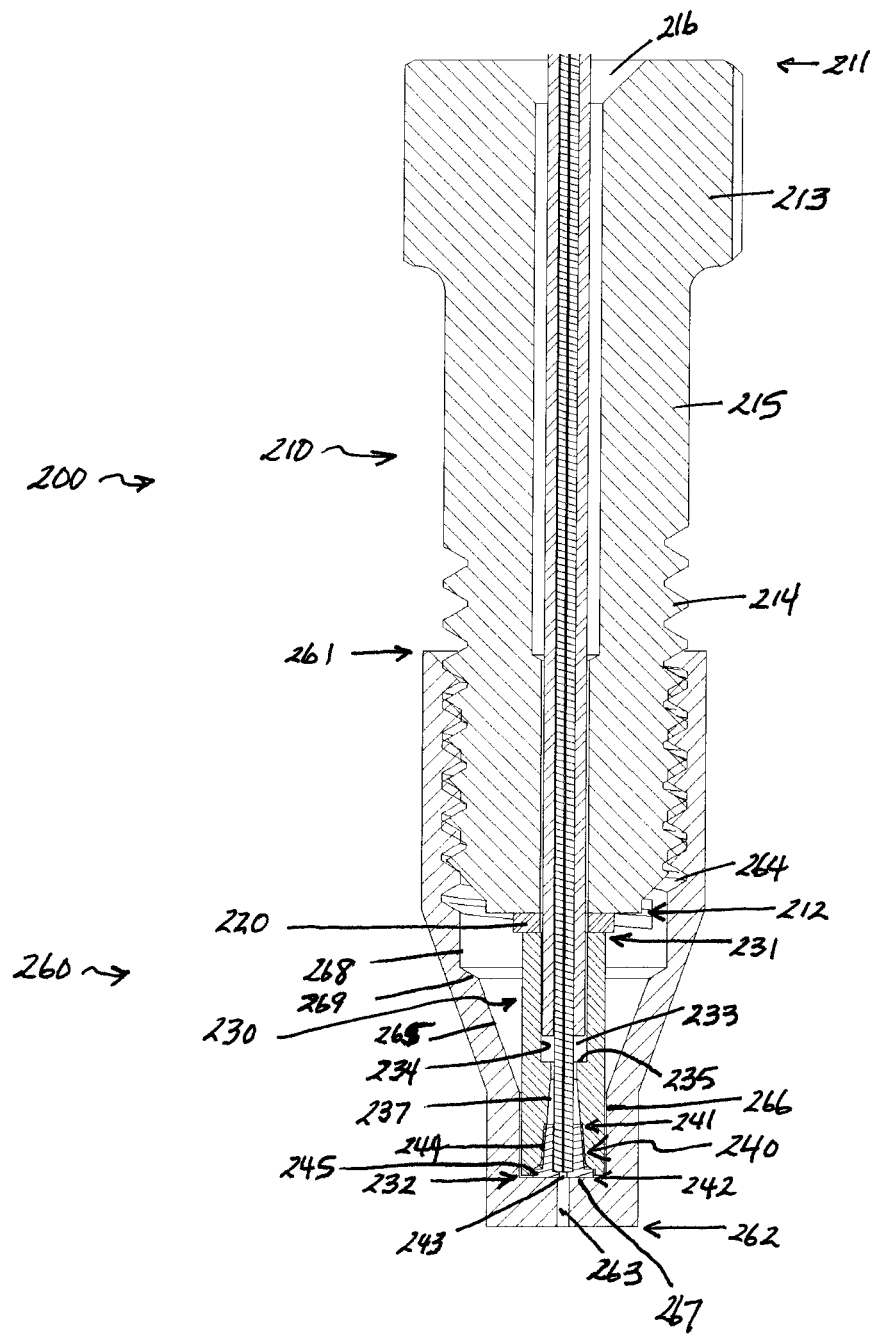
FIG. 15 is a cross-sectional view of the tube connection assembly of FIG. 13 upon complete engagement with the port.

FIG. 15 is a cross-sectional view of the assembly 200 shown in FIG. 11 upon further engagement with port 260, showing engagement of ferrule 240 with locktube 230. Nut 210 has a first end 211, a second end 212, a nut head 213, an externally non-threaded portion 215, an externally threaded portion 214, and internal passageway 216 that extends from the first end 211 to the second end 212 of the nut 210. Washer 220 defines internal passageway 221 (not clearly visible in FIG. 15). Locktube 230 comprises a first end 231 and a second end 232, an internal passageway 233 that extends from the first end 231 to the second end 232 of the locktube 230, a first internal non-tapered portion 234, a first internal lip 235, a second internal non-tapered portion 236 (not clearly visible in FIG. 15), an internal tapered portion 237, a second internal lip 238 (not clearly visible in FIG. 15), and a third internal non-tapered portion 239 (not clearly visible in FIG. 15). Ferrule 240 comprises a first end 241, a second end 242, an internal passageway 243 that extends from the first end 241 to the second end 242 of the ferrule 240, an externally tapered portion 244, an optional external protrusion 245, an internal lip 246 (not clearly visible in FIG. 15) and an external radius 247 (not clearly visible in FIG. 15). The internally tapered portion 237 of the locktube is adapted to receive and securely hold the externally tapered portion 244 of the ferrule 240 when the assembly 200 is assembled. Port 260 comprises a first end 261, second end 262, an internal passageway 263 that extends from the first end 261 to the second end 262 of the port 260, internally threaded portion 264, internal non-threaded portion 268, first internal tapered portion 269, second internal tapered portion 265, first internal non-tapered portion 266 and face 267. The externally threaded portion 214 of the nut 210 is adapted to be removably secured to the corresponding internally threaded portion 264 of the port 260, or a fitting, a union, or other component of an LC or other analytical instrument (AI) system (not shown).

Figure 16:
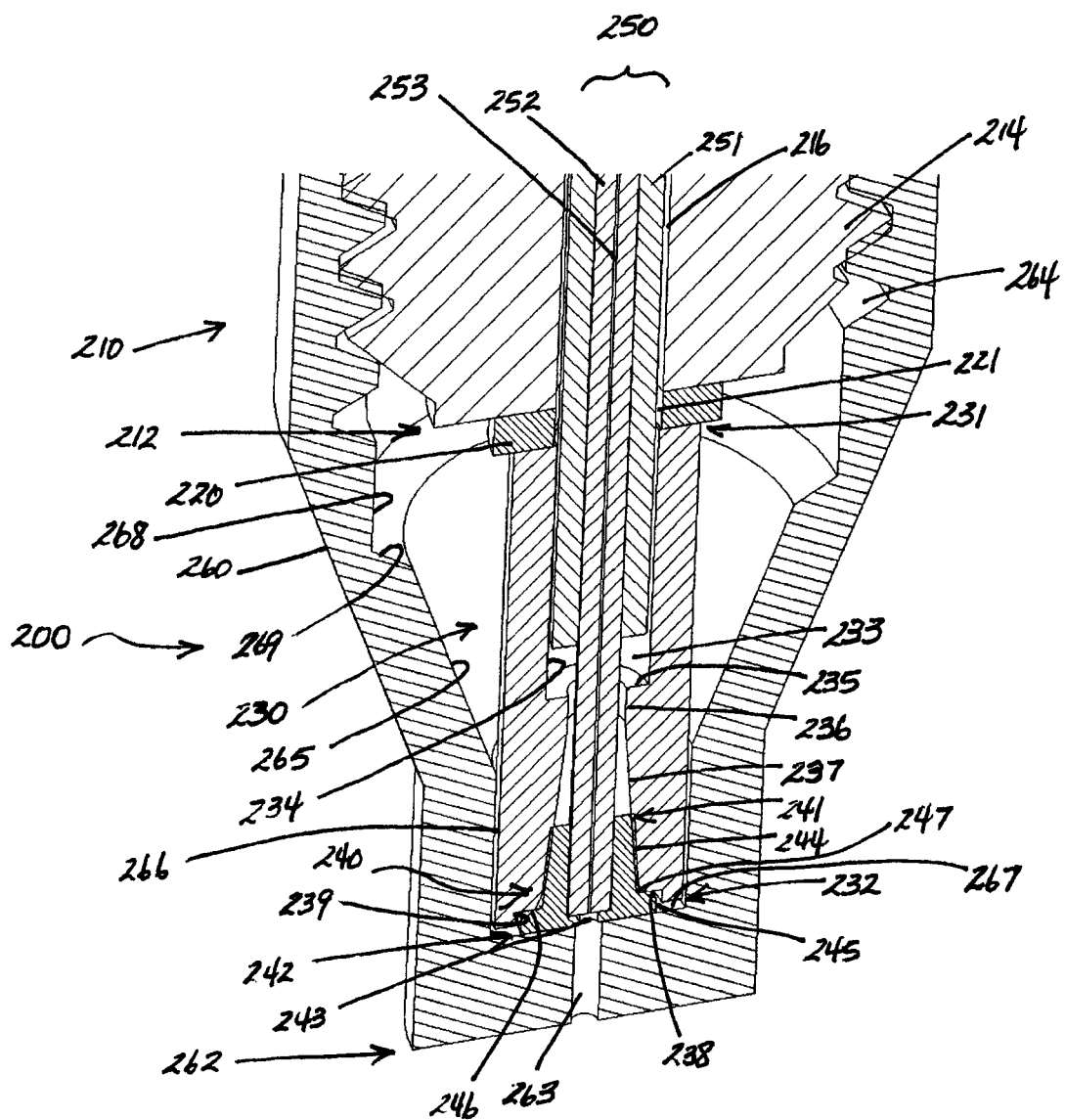
FIG. 16 is side perspective cross-sectional view of the bottom portion of the tube connection assembly of FIG. 13 upon complete engagement with the port.

FIG. 16 is a side perspective cross-sectional view of the lower portion of the assembly 200 and port 260 shown in FIG. 15. Nut 210 has a first end (not shown in FIG. 16), a second end 212, a nut head (not shown in FIG. 16), an externally non-threaded portion (not shown in FIG. 16), an externally threaded portion 214, and internal passageway 216 that extends from the first end (not shown in FIG. 16) to the second end 212 of the nut 210. Washer 220 defines internal passageway 221. Locktube 230 comprises a first end 231 and a second end 232, an internal passageway 233 that extends from the first end 231 to the second end 232 of the locktube 230, a first internal non-tapered portion 234, a first internal lip 235, a second internal non-tapered portion 236, an internal tapered portion 237, a second internal lip 238, and a third internal non-tapered portion 239. Ferrule 240 comprises a first end 241, a second end 242, an internal passageway 243 that extends from the first end 241 to the second end 242 of the ferrule 240, an externally tapered portion 244, an optional external protrusion 245, an internal lip 246 and an external radius 247. The internally tapered portion 237 of the locktube is adapted to receive and securely hold the externally tapered portion 244 of the ferrule 240 when the assembly 200 is assembled. Port 260 comprises a first end (not shown in FIG. 16), second end 262, an internal passageway 263 that extends from the first end (not shown in FIG. 16) to the second end 262 of the port 260, internally threaded portion 264, internal non-threaded portion 268, first internal tapered portion 269, second internal tapered portion 265, first internal non-tapered portion 266 and face 267. The externally threaded portion 214 of the nut 210 is adapted to be removably secured to the corresponding internally threaded portion 264 of the port 260, or a fitting, a union, or other component of an LC or other analytical instrument (AI) system (not shown).

Figure 17:
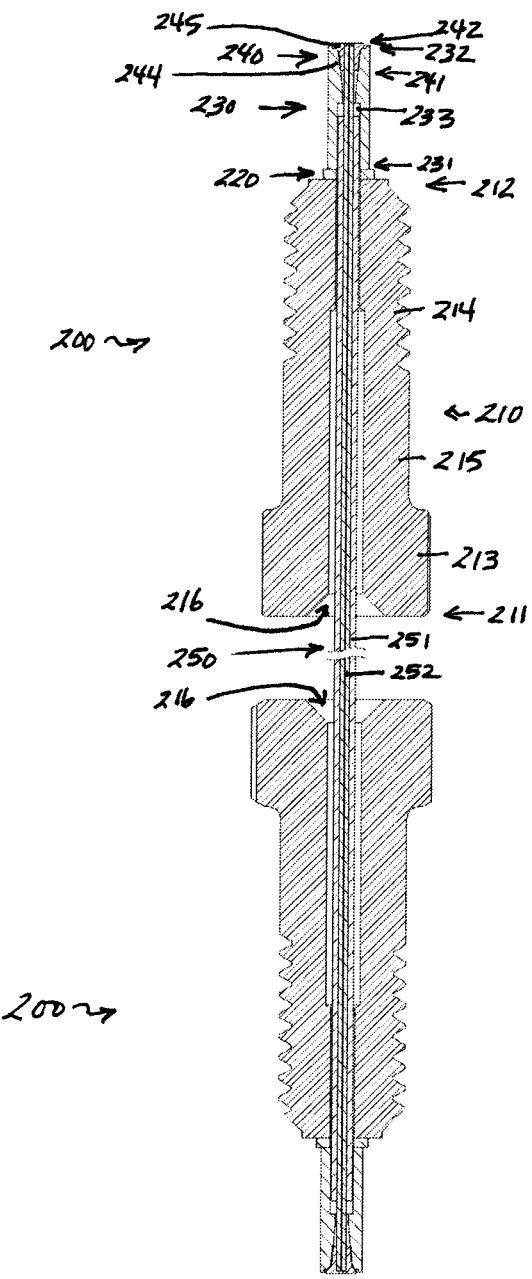
FIG. 17 is a cross-sectional view of the tube connection assembly of FIG. 13 with a second tube connection assembly at the other end of the tube.

FIG. 17 shows a cross-sectional view of the tube connection assembly 200 as shown in FIG. 12 with a second tube connection assembly 200 as shown in FIG. 12 at the other end of the tube 250. Assemblies 200 each include a nut 210, washer 220, locktube 230, ferrule 240 and tube 250. Nut 210 comprises first end 211 and second end 212, nut head 213, which is proximal to the first end 211 of the nut 210, an externally threaded portion 214 proximal to the other or second end 212 of the nut 210, externally non-threaded portion 215 between the nut head 213 and the externally threaded portion 214 and internal passageway 216 through the nut 210 from the first end 211 to the second end 212 of the nut 210. Washer 220 defines an internal passageway (not visible in FIG. 17). Locktube 230 comprises a first end 231, a second end 232, and defines an internal passageway 233 that extends from the first end 231 to the second end 232 of the locktube 230. Ferrule 240 comprises a first end 241 and a second end 242, and defines an internal passageway (not visible in FIG. 17) that extends from the first end 241 to the second end 242 of the ferrule 240. Ferrule 240 also comprises an external tapered portion 244 and an optional protrusion 245 proximal the second end 242 of the ferrule 240. The external tapered portion 244 of the ferrule 240 forms a truncated conical shape. Tube 250 comprises a strain relief tube 251 and an inner tube 252.

It will be appreciated that the nut 210, washer 220, locktube 230 and ferrule 240 in either or both of connection assemblies 200 can comprise a number of different materials. Nut 210, washer 220, locktube 230 and ferrule 240 can comprise a metal, such as stainless steel, or can comprise a polymer, such as a polyaryletherketone (PAEK), including, but not limited to, polyetherketone (PEK), polyetheretherketone (PEEK™), polyetherketoneketone (PEKK), polyetheretherketoneketone (PEEKK), and polyetherketoneetherketoneketone (PEKEKK). In addition, each of the components of either or both of connection assemblies 200 can comprise the same material, or some or all of the components can comprise different materials. It will be appreciated that a variety of metals and polymers may be selected for the components of either of both of connection assemblies 200 depending on the particular application, as that may involve a particular type of sample, a particular type of solvent, and/or a particular pressure range. In addition, the selection of materials for the tube 250, such as PEEK™, PEEKsil™, metal, including, but not limited to, stainless steel, titanium, nickel or gold, coated metal, or fused silica, may lead to a selection of a particular material for the components of either or both of connection assemblies 200. In addition, PEEK™ (or other polymers) may be used that is reinforced with carbon, carbon fibers, glass fibers, or steel fibers, or the like. Other polymer materials which may be used include, but are not limited to, TEFLON®, TEFZEL®, DELRIN®, polyphenylene sulfide (PPS), polypropylene, and others, depending on the foregoing factors and perhaps others, such as cost. Those skilled in the art will further appreciate that either or both of connection assemblies 200 is shown for connecting tube 250 to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

Figure 18:
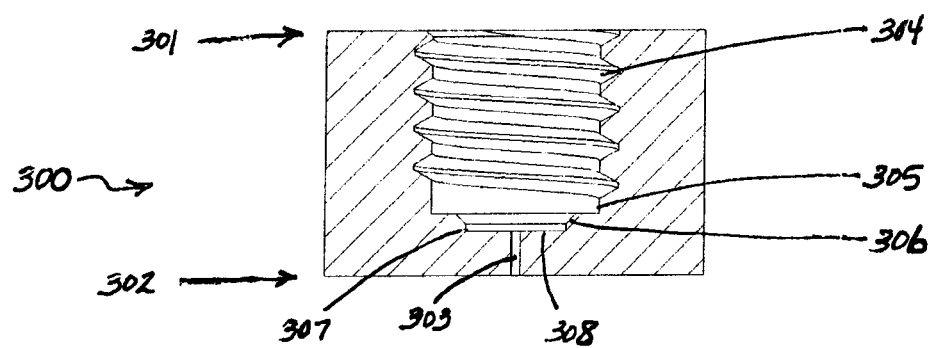
FIG. 18 is a cross-sectional view of an embodiment of a port in accordance with one aspect of the present disclosure.

Referring now to FIG. 18, a cross-sectional view of an embodiment of a port 300 of the present disclosure is shown. As shown in FIG. 18, the port 300 comprises a first end 301 a second end 302, an internal passageway 303 that extends from the first end 301 to the second end 302 of the port 300, an internally threaded portion 304, an optional first internal non-tapered portion 305, an internal tapered portion 306, an optional second internal non-tapered portion 307 and a face 308. Port 300 is generally circular and symmetric about a center axis. As detailed herein, the externally threaded portion of a fitting (not shown) is adapted to be removably secured to the corresponding internally threaded portion 304 of the port 300. The use of internal threads on one element, such as the port 300, versus external threads, is a matter of selection. Those skilled in the art will therefore appreciate that the port 300 in an alternative embodiment could have external threads (not shown) that could be engaged with internal threads (not shown) of a fitting (not shown).

Figure 19:
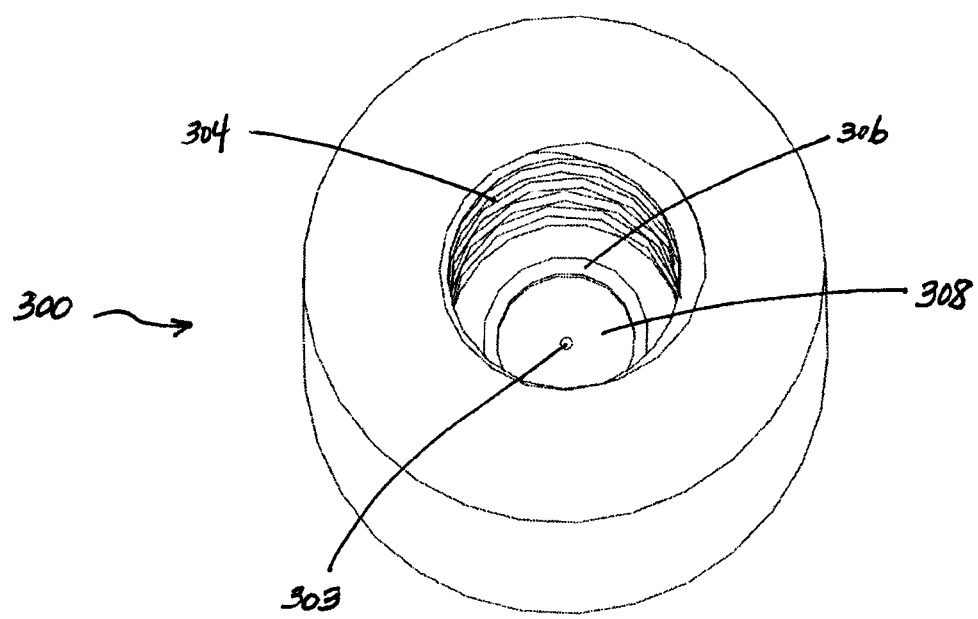
FIG. 19 is a top perspective view of the port shown in FIG. 18.

FIG. 19 shows a top perspective view of the port 300 shown in FIG. 18. Portions of the port 300 that are visible in FIG. 17 include internal passageway 303. Internally threaded portion 304 internal tapered portion 306 and face 308.

It will be appreciated that the port 300 can comprise a metal, such as stainless steel, or can comprise a polymer, such as a polyaryletherketone (PAEK), including, but not limited to, polyetherketone (PEK), polyetheretherketone (PEEK™), polyetherketoneketone (PEKK), polyetheretherketoneketone (PEEKK), and polyetherketoneetherketoneketone (PEKEKK), or a combination thereof. It will be appreciated that a variety of metals and polymers may be selected for the port 300 depending on the particular application, as that may involve a particular type of sample, a particular type of solvent, and/or a particular pressure range. In addition, the selection of materials for the tube (not shown), such as PEEK™, PEEKsil™, stainless steel, or fused silica, may lead to a selection of a particular material for the port 300. In addition, PEEK™ (or other polymers) may be used that is reinforced with carbon, carbon fibers, glass fibers, or steel fibers, or the like. Other polymer materials which may be used include, but are not limited to, TEFLON®, TEFZEL®, DELRIN®, polyphenylene sulfide (PPS), polypropylene, and others, depending on the foregoing factors and perhaps others, such as cost. Those skilled in the art will appreciate that port 300 is designed to provide a much shallower port, generally with a depth of less than about 0.4 inches, and thus require less space on an AI or LC system, or component of an AI or LC system, than conventional ports (not shown), as described more fully below. Furthermore, port 300 is easier, faster and less expensive to manufacture than conventional ports (not shown).

Figure 20:
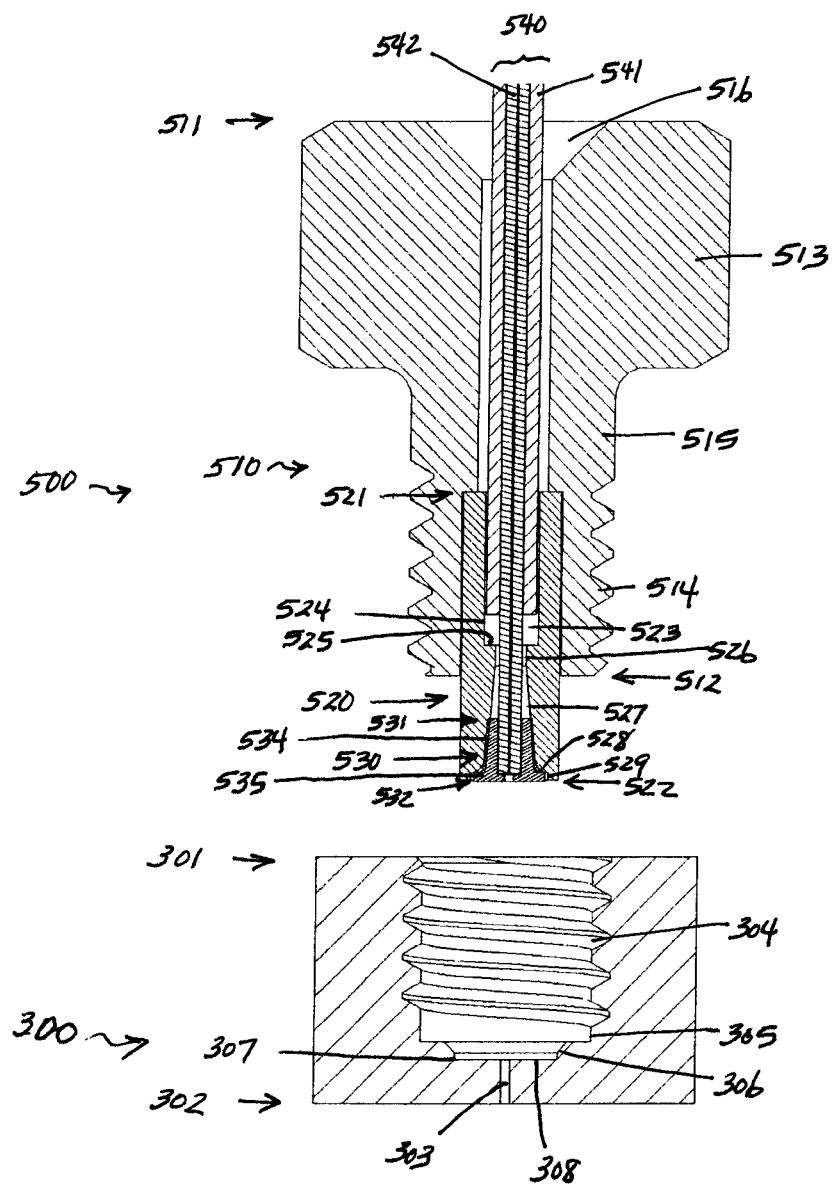
FIG. 20 is a cross-sectional view of the port of FIG. 18 and an alternate embodiment of a tube connection assembly in accordance with another aspect of the present disclosure.

FIG. 20 is an exploded cross-sectional view of the port 300 of FIG. 18 and an alternate embodiment of a tube connection assembly 500 in accordance with another aspect of the present disclosure. Assembly 500 includes a nut 510, locktube 520, ferrule 530 and tube 540. Nut 510 comprises first end 511 and second end 512, nut head 513, which is proximal to the first end 511 of the nut 510, an externally threaded portion 514 proximal to the other or second end 512 of the nut 510, externally non-threaded portion 515 between the nut head 513 and the externally threaded portion 514 and internal passageway 516 through the nut 510 from the first end 511 to the second end 512 of the nut 510, which broadens proximal the second end 512 to engage with locktube 520. Locktube 520 comprises a first end 521 and a second end 522, an internal passageway 523 that extends from the first end 521 to the second end 522 of the locktube 520, a first internal non-tapered portion 524, a first internal lip 525, a second internal non-tapered portion 526, an internal tapered portion 527, a second internal lip 528, and a third internal non-tapered portion 529. Ferrule 530 comprises a first end 531 and a second end 532, and defines an internal passageway (not visible in FIG. 20) that extends from the first end 531 to the second end 532 of the ferrule 530. Ferrule 530 also comprises an external tapered portion 534 and an optional protrusion 535 proximal the second end 532 of the ferrule 530. The external tapered portion 534 of the ferrule 530 forms a truncated conical shape. Tube 540 comprises a strain relief tube 541 and an inner tube 542, and defines an internal passageway (not clearly visible in FIG. 20) running through the entire length of tube 540. Port 300 once again comprises a first end 301 a second end 302, an internal passageway 303 that extends from the first end 301 to the second end 302 of the port 300, an internally threaded portion 304, a first internal non-tapered portion 305, an internal tapered portion 306, a second internal non-tapered portion 307 and a face 308.

Figure 21:
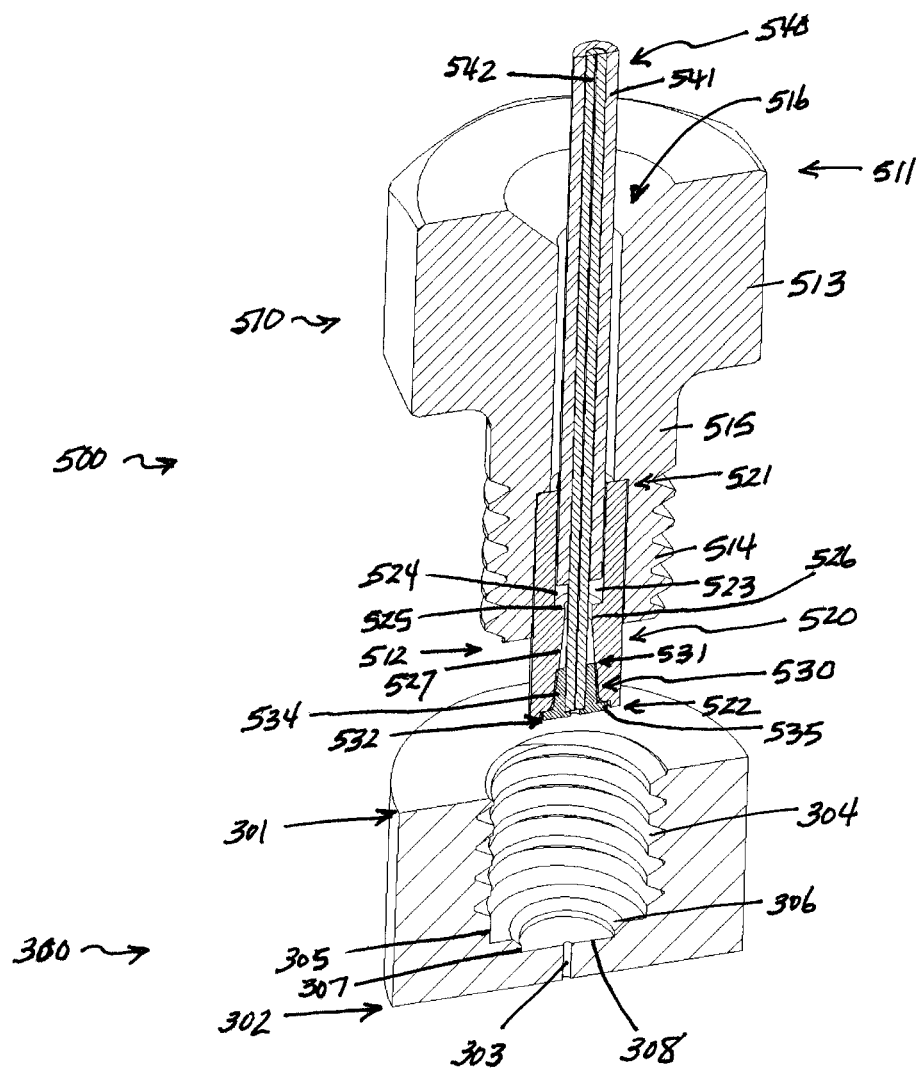
FIG. 21 is an exploded top side perspective cross-sectional view of the port and tube connection assembly of FIG. 20.

FIG. 21 is an exploded side perspective cross-sectional view of the port 300 and tube connection assembly 500 of FIG. 20. Assembly 500 once again includes a nut 510, locktube 520, ferrule 530 and tube 540. Nut 510 comprises first end 511 and second end 512, nut head 513, which is proximal to the first end 511 of the nut 510, an externally threaded portion 514 proximal to the other or second end 512 of the nut 510, externally non-threaded portion 515 between the nut head 513 and the externally threaded portion 514 and internal passageway 516 through the nut 510 from the first end 511 to the second end 512 of the nut 510, which broadens proximal the second end 512 to engage with locktube 520. Locktube 520 comprises a first end 521 and a second end 522, an internal passageway 523 that extends from the first end 521 to the second end 522 of the locktube 520, a first internal non-tapered portion 524, a first internal lip 525, a second internal non-tapered portion 526, an internal tapered portion 527, a second internal lip 528 (not clearly visible in FIG. 21), and a third internal non-tapered portion 529 (not clearly visible in FIG. 21). Ferrule 530 comprises a first end 531 and a second end 532, and defines an internal passageway (not clearly visible in FIG. 21) that extends from the first end 531 to the second end 532 of the ferrule 530. Ferrule 530 also comprises an external tapered portion 534 and an optional protrusion 535 proximal the second end 532 of the ferrule 530. The external tapered portion 534 of the ferrule 530 forms a truncated conical shape. Tube 540 comprises a strain relief tube 541 and an inner tube 542, and defines an internal passageway (not clearly visible in FIG. 21) running through the entire length of tube 540. Port 300 once again comprises a first end 301 a second end 302, an internal passageway 303 that extends from the first end 301 to the second end 302 of the port 300, an internally threaded portion 304, a first internal non-tapered portion 305, an internal tapered portion 306, a second internal non-tapered portion 307 and a face 308.

Figure 22:
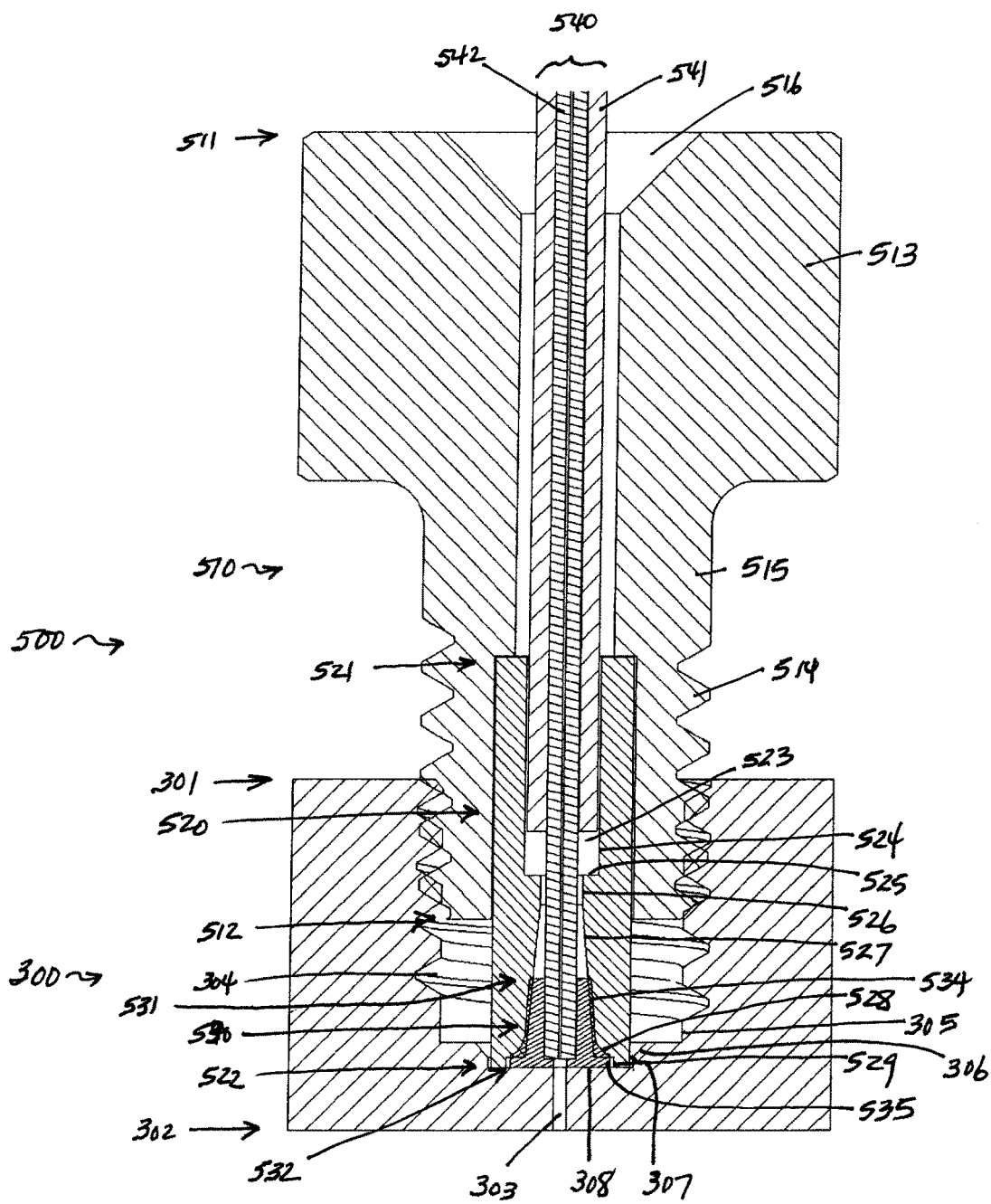
FIG. 22 is a cross-sectional view of the port and tube connection assembly of FIG. 20 upon engagement.

FIG. 22 is a cross-sectional view of the port 300 and tube connection assembly 500 of FIG. 20 upon engagement. Assembly 500 once again includes a nut 510, locktube 520, ferrule 530 and tube 540. Nut 510 comprises first end 511 and second end 512, nut head 513, which is proximal to the first end 511 of the nut 510, an externally threaded portion 514 proximal to the other or second end 512 of the nut 510, externally non-threaded portion 515 between the nut head 513 and the externally threaded portion 514 and internal passageway 516 through the nut 510 from the first end 511 to the second end 512 of the nut 510, which broadens proximal the second end 512 to engage with locktube 520. Locktube 520 comprises a first end 521 and a second end 522, an internal passageway 523 that extends from the first end 521 to the second end 522 of the locktube 520, a first internal non-tapered portion 524, a first internal lip 525, a second internal non-tapered portion 526, an internal tapered portion 527, a second internal lip 528, and a third internal non-tapered portion 529. Ferrule 530 comprises a first end 531 and a second end 532, and defines an internal passageway (not visible in FIG. 22) that extends from the first end 531 to the second end 532 of the ferrule 530. Ferrule 530 also comprises an external tapered portion 534 and an optional protrusion 535 proximal the second end 532 of the ferrule 530. The external tapered portion 534 of the ferrule 530 forms a truncated conical shape. Tube 540 comprises a strain relief tube 541 and an inner tube 542. Port 300 once again comprises a first end 301 a second end 302, an internal passageway 303 that extends from the first end 301 to the second end 302 of the port 300, an internally threaded portion 304, a first internal non-tapered portion 305, an internal tapered portion 306, a second internal non-tapered portion 307 and a face 308. The externally threaded portion 514 of the nut 510 is adapted to be removably secured to the corresponding internally threaded portion 304 of the port 300, or a fitting, a union, or other component of an LC or other analytical instrument (AI) system (not shown).

Figure 23:
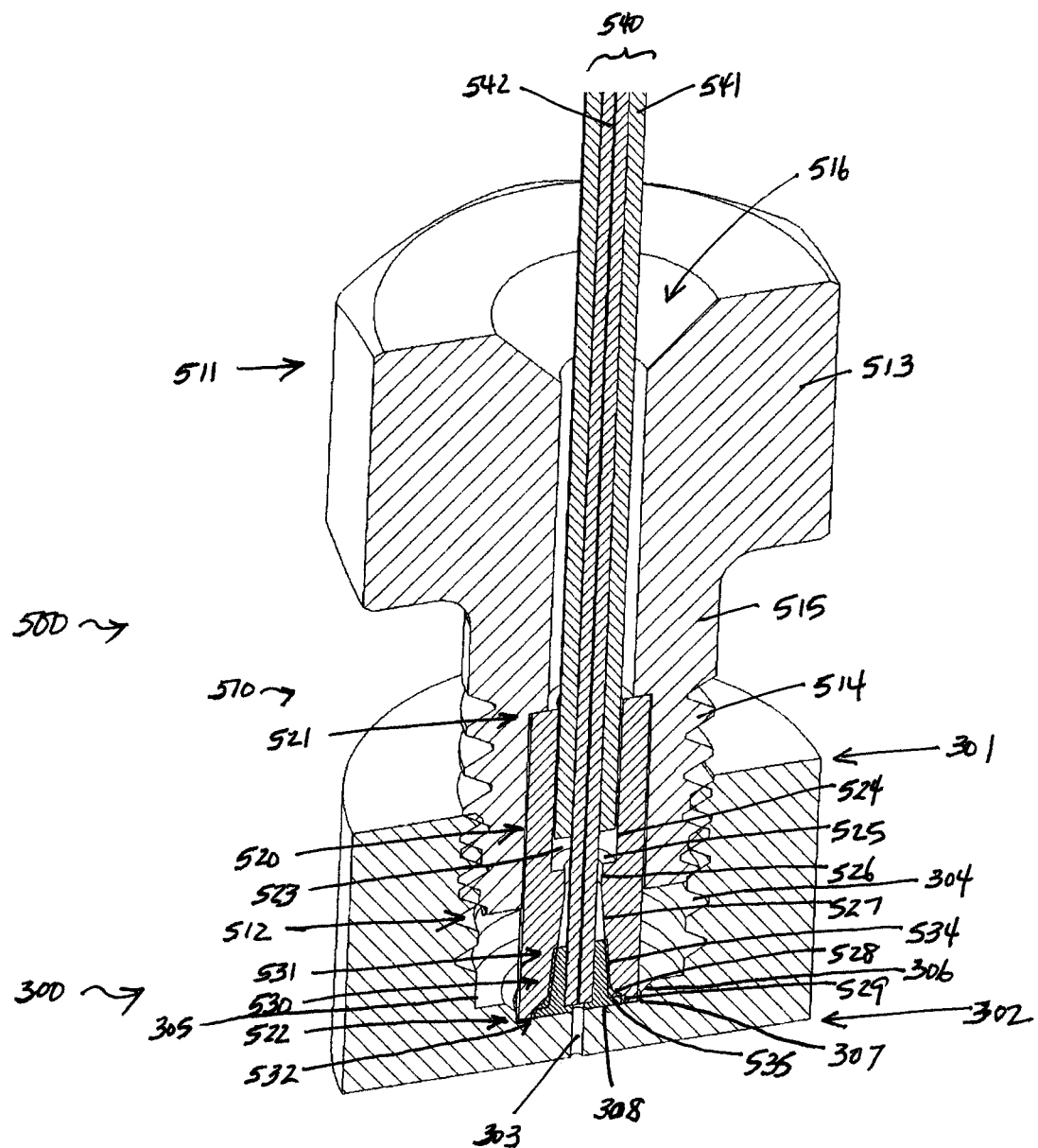
FIG. 23 is a top side perspective cross-sectional view of the port and tube connection assembly of FIG. 20 upon engagement.

FIG. 23 is a side perspective cross-sectional view of the port 300 and tube connection assembly 500 of FIG. 21 upon engagement. Assembly 500 once again includes a nut 510, locktube 520, ferrule 530 and tube 540. Nut 510 comprises first end 511 and second end 512, nut head 513, which is proximal to the first end 511 of the nut 510, an externally threaded portion 514 proximal to the other or second end 512 of the nut 510, externally non-threaded portion 515 between the nut head 513 and the externally threaded portion 514 and internal passageway 516 through the nut 510 from the first end 511 to the second end 512 of the nut 510, which broadens proximal the second end 512 to engage with locktube 520. Locktube 520 comprises a first end 521 and a second end 522, an internal passageway 523 that extends from the first end 521 to the second end 522 of the locktube 520, a first internal non-tapered portion 524, a first internal lip 525, an optional second internal non-tapered portion 526, an internal tapered portion 527, a second internal lip 528, and a third internal non-tapered portion 529. Ferrule 530 comprises a first end 531 and a second end 532, and defines an internal passageway (not visible in FIG. 23) that extends from the first end 531 to the second end 532 of the ferrule 530. Ferrule 530 also comprises an external tapered portion 534 and an optional protrusion 535 proximal the second end 532 of the ferrule 530. The external tapered portion 534 of the ferrule 530 forms a truncated conical shape. Tube 540 comprises a strain relief tube 541 and an inner tube 542. Port 300 once again comprises a first end 301 a second end 302, an internal passageway 303 that extends from the first end 301 to the second end 302 of the port 300, an internally threaded portion 304, a first internal non-tapered portion 305, an internal tapered portion 306, a second internal non-tapered portion 307 and a face 308. The externally threaded portion 514 of the nut 510 is adapted to be removably secured to the corresponding internally threaded portion 304 of the port 300, or a fitting, a union, or other component of an LC or other analytical instrument (AI) system (not shown).

Figure 24:
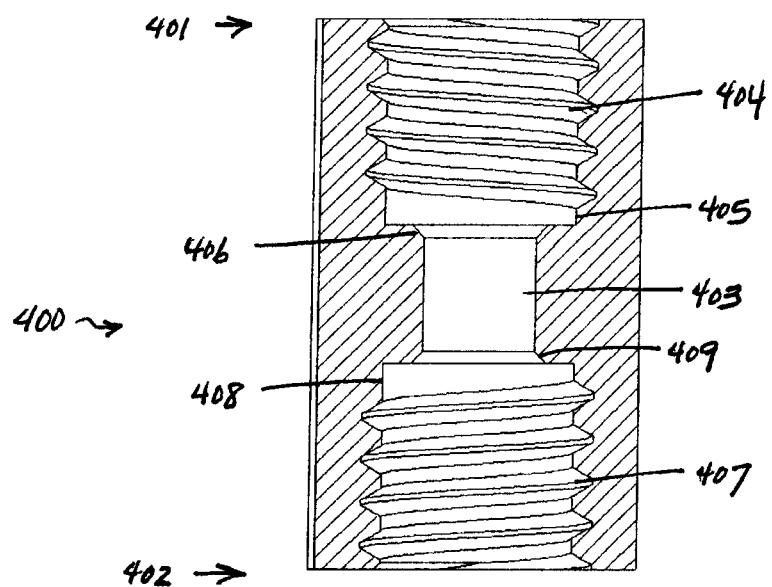
FIG. 24 is a cross-sectional view of an embodiment of a union in accordance with one aspect of the present disclosure.

Referring now to FIG. 24, a cross-sectional view of an embodiment of a union 400 of the present disclosure is shown. As shown in FIG. 24, the union 400 comprises a first end 401 a second end 402, an internal passageway 403 that extends from the first end 401 to the second end 402 of the union 400, a first internally threaded portion 404, a first internal non-tapered portion 405, and a first internal tapered portion 406 proximal to the first end 401 of the union 400, and a second internally threaded portion 407, a second internal non-tapered portion 408, and a second internal tapered portion 409 proximal to the second end 402 of the union 400. Union 400 is generally circular and symmetric about a center axis. As detailed herein, the externally threaded portion of one or two fittings (not shown) are adapted to be removably secured to the corresponding first internally threaded portion 404 and second internally threaded portion 407 of the union 400. The use of internal threads on one element, such as the union 400, versus external threads, is a matter of selection. Those skilled in the art will therefore appreciate that the union 400 in an alternative embodiment could have external threads (not shown) that could be engaged with internal threads (not shown) of a fitting (not shown).

Figure 25:
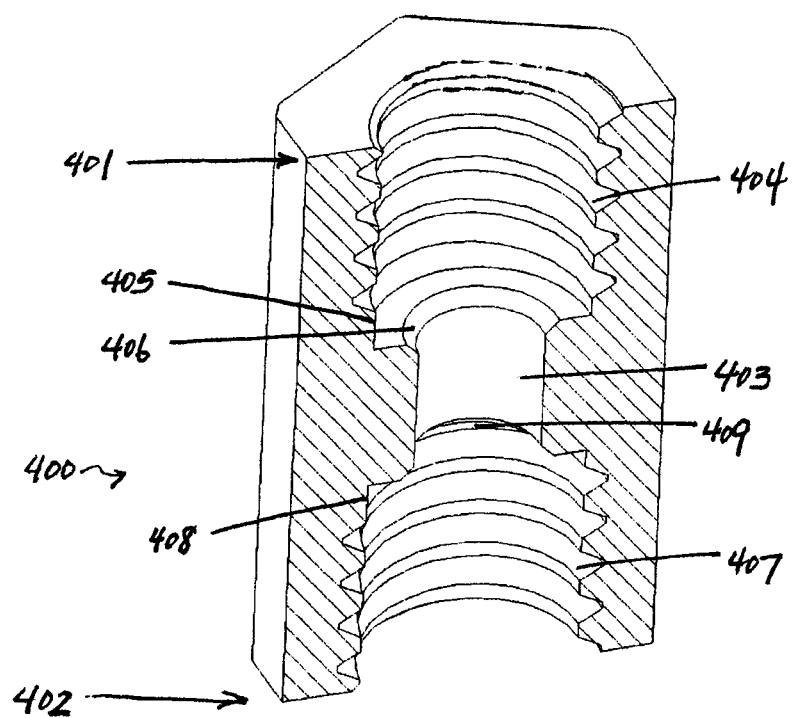
FIG. 25 is a top perspective cross-sectional view of the union shown in FIG. 24.

FIG. 25 shows a top perspective view of the union 400 shown in FIG. 24. As shown in FIG. 25, the union 400 comprises a first end 401 a second end 402, an internal passageway 403 that extends from the first end 401 to the second end 402 of the union 400, a first internally threaded portion 404, a first internal non-tapered portion 405, and a first internal tapered portion 406 proximal to the first end 401 of the union 400, and a second internally threaded portion 407, a second internal non-tapered portion 408, and a second internal tapered portion 409 proximal to the second end 402 of the union 400.

It will be appreciated that the union 400 can comprise a metal, such as stainless steel, or can comprise a polymer, such as a polyaryletherketone (PAEK), including, but not limited to, polyetherketone (PEK), polyetheretherketone (PEEK™), polyetherketoneketone (PEKK), polyetheretherketoneketone (PEEKK), and polyetherketoneetherketoneketone (PEKEKK), or a combination thereof. It will be appreciated that a variety of metals and polymers may be selected for the union 400 depending on the particular application, as that may involve a particular type of sample, a particular type of solvent, and/or a particular pressure range. In addition, the selection of materials for the tube (not shown), such as PEEK™, PEEKsil™, stainless steel, or fused silica, may lead to a selection of a particular material for the union 400. In addition, PEEK™ (or other polymers) may be used that is reinforced with carbon, carbon fibers, glass fibers, or steel fibers, or the like. Other polymer materials which may be used include, but are not limited to, TEFLON®, TEFZEL®, DELRIN®, polyphenylene sulfide (PPS), polypropylene, and others, depending on the foregoing factors and perhaps others, such as cost. Those skilled in the art will appreciate that union 400 is designed to provide a much shallower union, generally with a depth of less than about 0.4 inches, and thus require less space on an AI or LC system, or component of an AI or LC system, than conventional unions (not shown), as described more fully below. Furthermore, union 400 is easier, faster and less expensive to manufacture than conventional unions (not shown).

Figure 26:
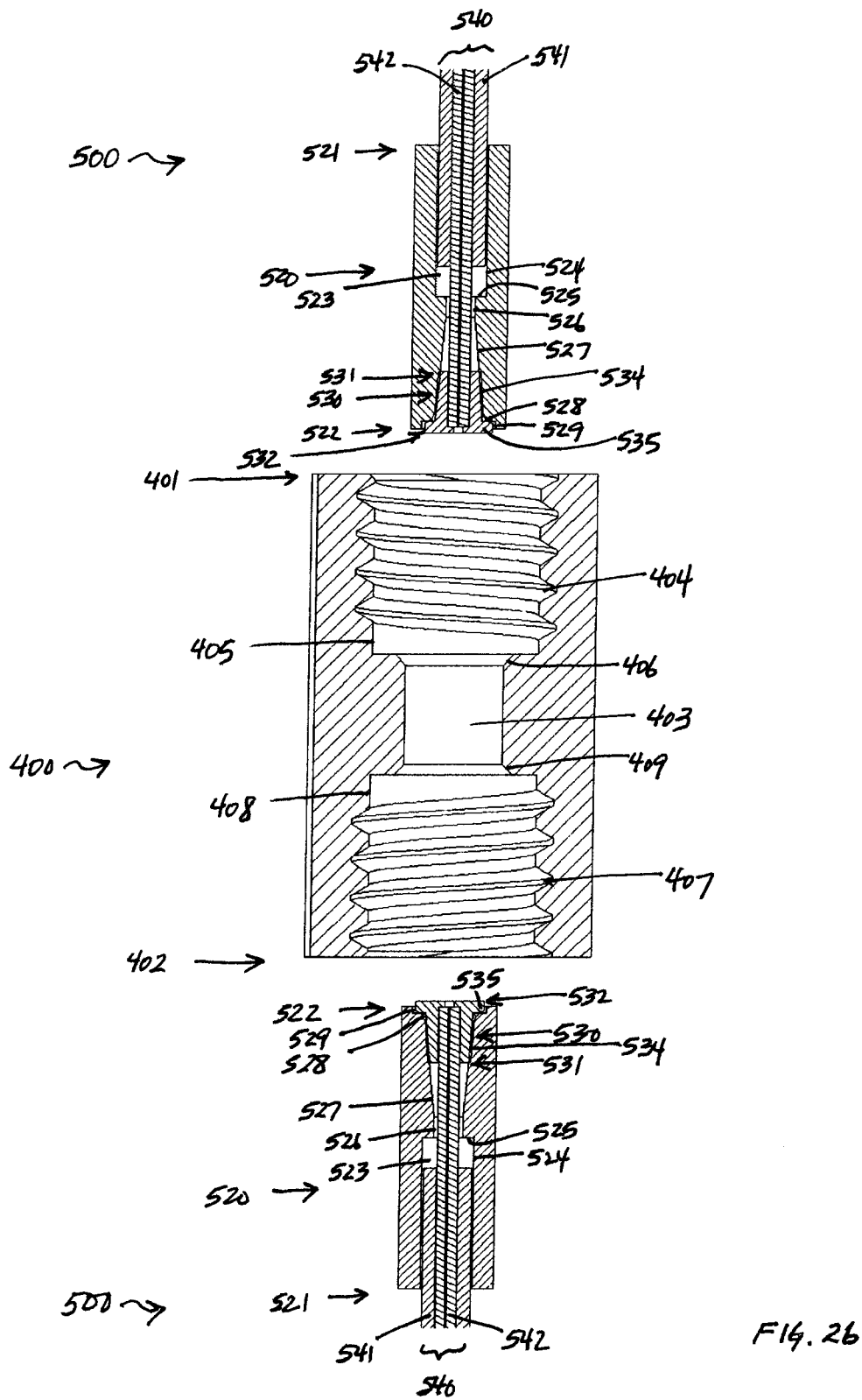
FIG. 26 is an exploded cross-sectional view of the union as shown in FIG. 24 with the lower portion of two tube connection assemblies as shown in FIG. 20.

FIG. 26 is an exploded cross-sectional view of the union 400 as shown in FIG. 24 with the lower portion of two tube connection assemblies 500 as shown in FIG. 20. Assemblies 500 each include a nut (not shown in FIG. 26), locktube 520, ferrule 530 and tube 540. Locktube 520 comprises a first end 521 and a second end 522, an internal passageway 523 that extends from the first end 521 to the second end 522 of the locktube 520, a first internal non-tapered portion 524, a first internal lip 525, a second internal non-tapered portion 526, an internal tapered portion 527, a second internal lip 528, and a third internal non-tapered portion 529. Ferrule 530 comprises a first end 531 and a second end 532, and defines an internal passageway (not visible in FIG. 26) that extends from the first end 531 to the second end 532 of the ferrule 530. Ferrule 530 also comprises an external tapered portion 534 and an optional protrusion 535 proximal the second end 532 of the ferrule 530. The external tapered portion 534 of the ferrule 530 forms a truncated conical shape. Tube 540 comprises a strain relief tube 541 and an inner tube 542. Union 400 comprises a first end 401 a second end 402, an internal passageway 403 that extends from the first end 401 to the second end 402 of the union 400, a first internally threaded portion 404, a first internal non-tapered portion 405, and a first internal tapered portion 406 proximal to the first end 401 of the union 400, and a second internally threaded portion 407, a second internal non-tapered portion 408, and a second internal tapered portion 409 proximal to the second end 402 of the union 400.

Figure 27:
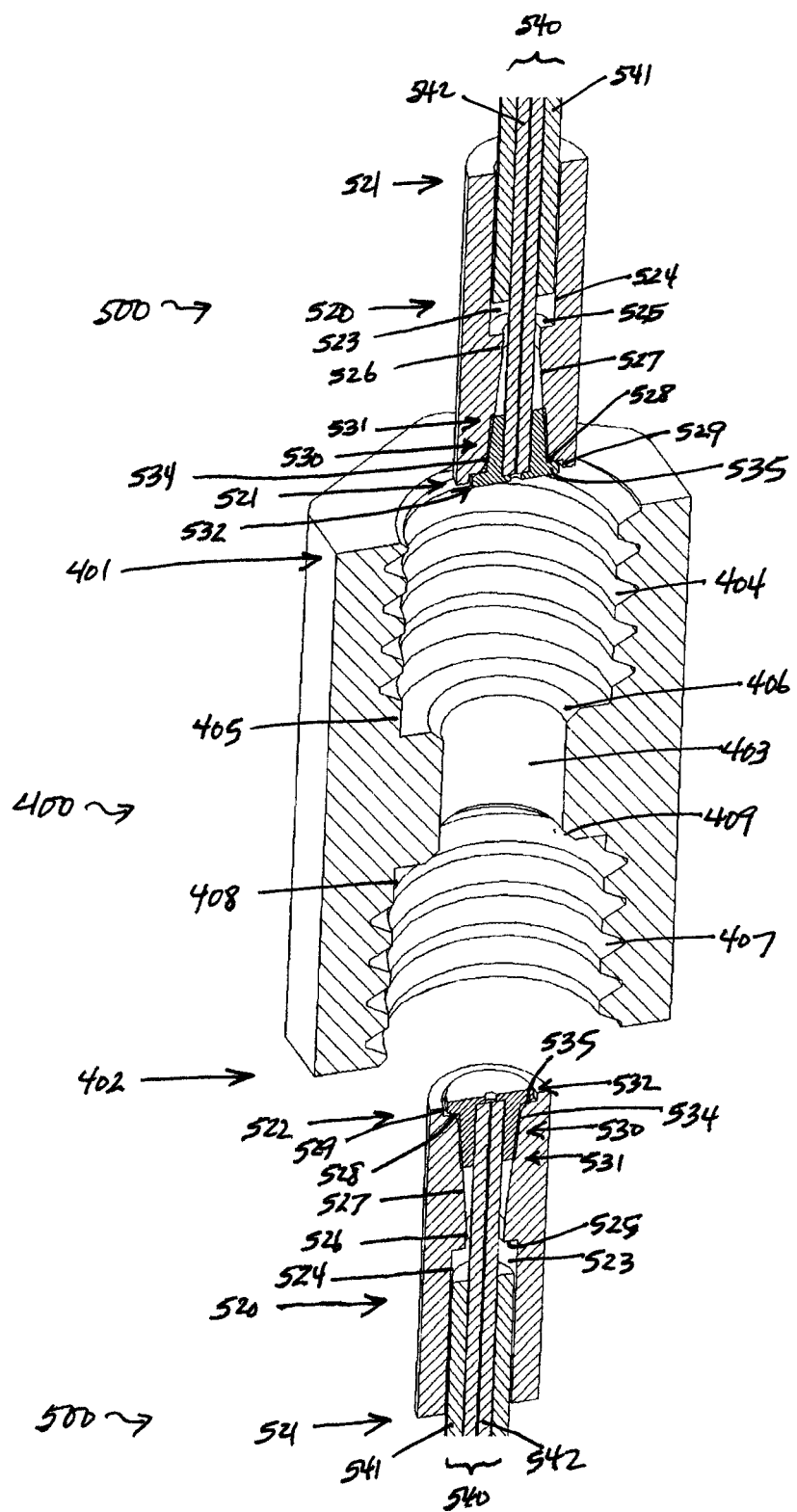
FIG. 27 is a top side perspective cross-sectional view of the union as shown in FIG. 24 with the lower portion of two tube connection assemblies as shown in FIG. 20.

FIG. 27 is a side perspective cross-sectional view of the union 400 as shown in FIG. 24 with the lower portion of two tube connection assemblies as shown in FIG. 20. Assemblies 500 each include a nut (not shown in FIG. 27), locktube 520, ferrule 530 and tube 540. Locktube 520 comprises a first end 521 and a second end 522, an internal passageway 523 that extends from the first end 521 to the second end 522 of the locktube 520, a first internal non-tapered portion 524, a first internal lip 525, a second internal non-tapered portion 526, an internal tapered portion 527, a second internal lip 528, and a third internal non-tapered portion 529. Ferrule 530 comprises a first end 531 and a second end 532, and defines an internal passageway (not visible in FIG. 27) that extends from the first end 531 to the second end 532 of the ferrule 530. Ferrule 530 also comprises an external tapered portion 534 and an optional protrusion 535 proximal the second end 532 of the ferrule 530. The external tapered portion 534 of the ferrule 530 forms a truncated conical shape. Tube 540 comprises a strain relief tube 541 and an inner tube 542. Union 400 comprises a first end 401 a second end 402, an internal passageway 403 that extends from the first end 401 to the second end 402 of the union 400, a first internally threaded portion 404, a first internal non-tapered portion 405, and a first internal tapered portion 406 proximal to the first end 401 of the union 400, and a second internally threaded portion 407, a second internal non-tapered portion 408, and a second internal tapered portion 409 proximal to the second end 402 of the union 400.

Figure 28:
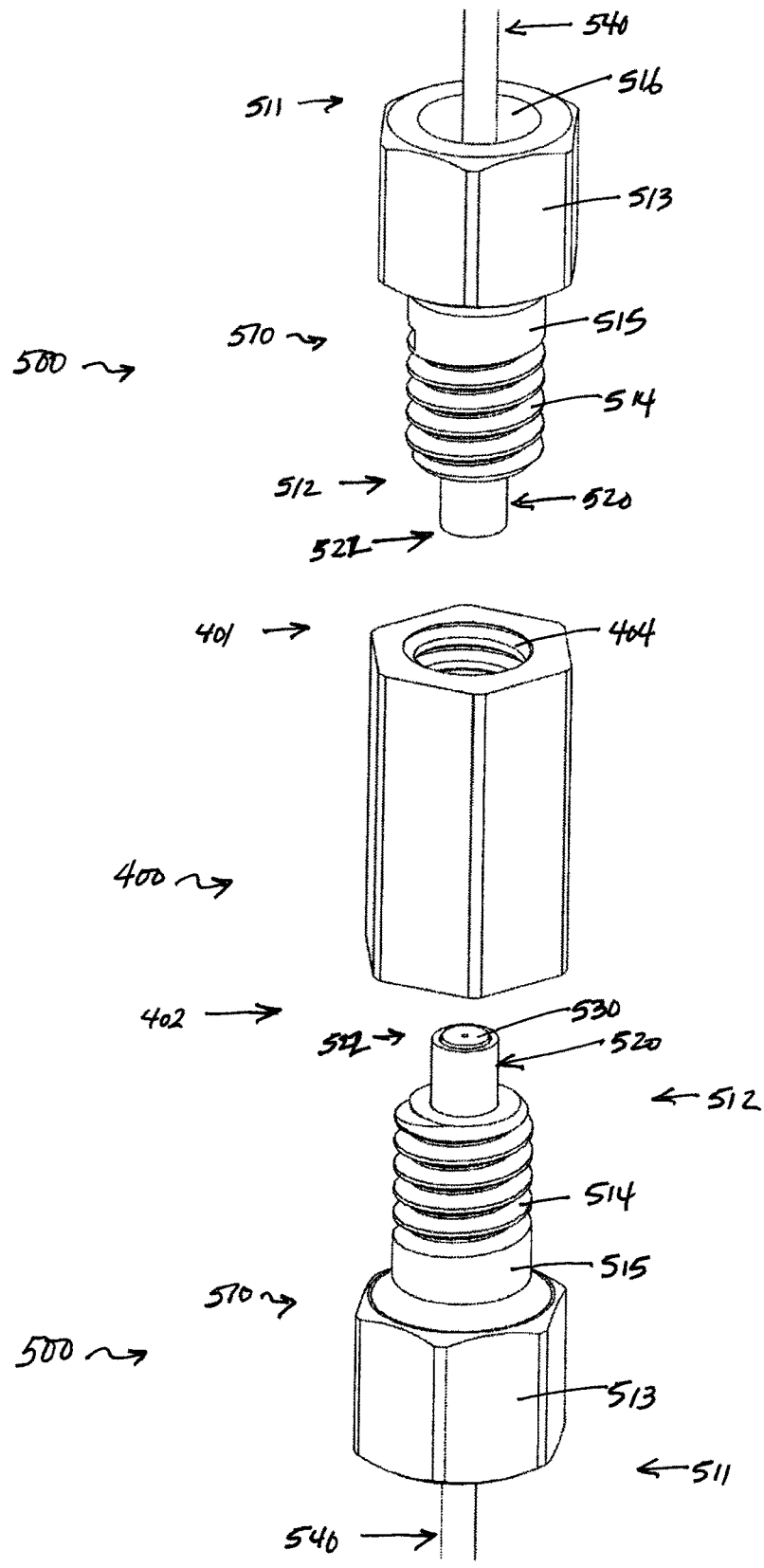
FIG. 28 is a top perspective side view of the union as shown in FIG. 24 and two tube connection assemblies as shown in FIG. 20.

FIG. 28 is a top perspective side view of the union 400 as shown in FIG. 24 and two tube connection assemblies 500 as shown in FIG. 20. Visible in FIG. 28 are assemblies 500, which each include a nut 510, locktube 520, ferrule 530 and tube 540. Nut 510 comprises first end 511 and second end 512, nut head 513, which is proximal to the first end 511 of the nut 510, an externally threaded portion 514 proximal to the other or second end 512 of the nut 510, externally non-threaded portion 515 between the nut head 513 and the externally threaded portion 514 and internal passageway 516 through the nut 510 from the first end 511 to the second end 512 of the nut 510, which broadens (not shown in FIG. 28) proximal the second end 512 to engage with locktube 520. Locktube 520 comprises a first end (not visible in FIG. 28) and a second end 522, an internal passageway (not visible in FIG. 28) that extends from the first end (not visible in FIG. 28) to the second end 522 of the locktube 520, a first internal non-tapered portion (not visible in FIG. 28), a first internal lip (not visible in FIG. 28), a second internal non-tapered portion (not visible in FIG. 28), an internal tapered portion (not visible in FIG. 28), a second internal lip (not visible in FIG. 28), and a third internal non-tapered portion (not visible in FIG. 28). Ferrule 530 comprises a first end (not visible in FIG. 28) and a second end (not visible in FIG. 28), and defines an internal passageway (not visible in FIG. 28) that extends from the first end (not visible in FIG. 28) to the second end (not visible in FIG. 28) of the ferrule 530. Ferrule 530 also comprises an external tapered portion (not visible in FIG. 28) and an optional protrusion (not visible in FIG. 28) proximal the second end (not visible in FIG. 28) of the ferrule 530. The external tapered portion (not visible in FIG. 28) of the ferrule 530 forms a truncated conical shape. Tube 540 comprises a strain relief tube (not visible in FIG. 28) and an inner tube (not visible in FIG. 28). Union 400 comprises a first end 401 a second end 402, an internal passageway (not visible in FIG. 28) that extends from the first end 401 to the second end 402 of the union 400, a first internally threaded portion 404, a first internal non-tapered portion (not visible in FIG. 28), and a first internal tapered portion (not visible in FIG. 28) proximal to the first end 401 of the union 400, and a second internally threaded portion (not visible in FIG. 28), a second internal non-tapered portion (not visible in FIG. 28), and a second internal tapered portion (not visible in FIG. 28) proximal to the second end 402 of the union 400.

Figure 29:
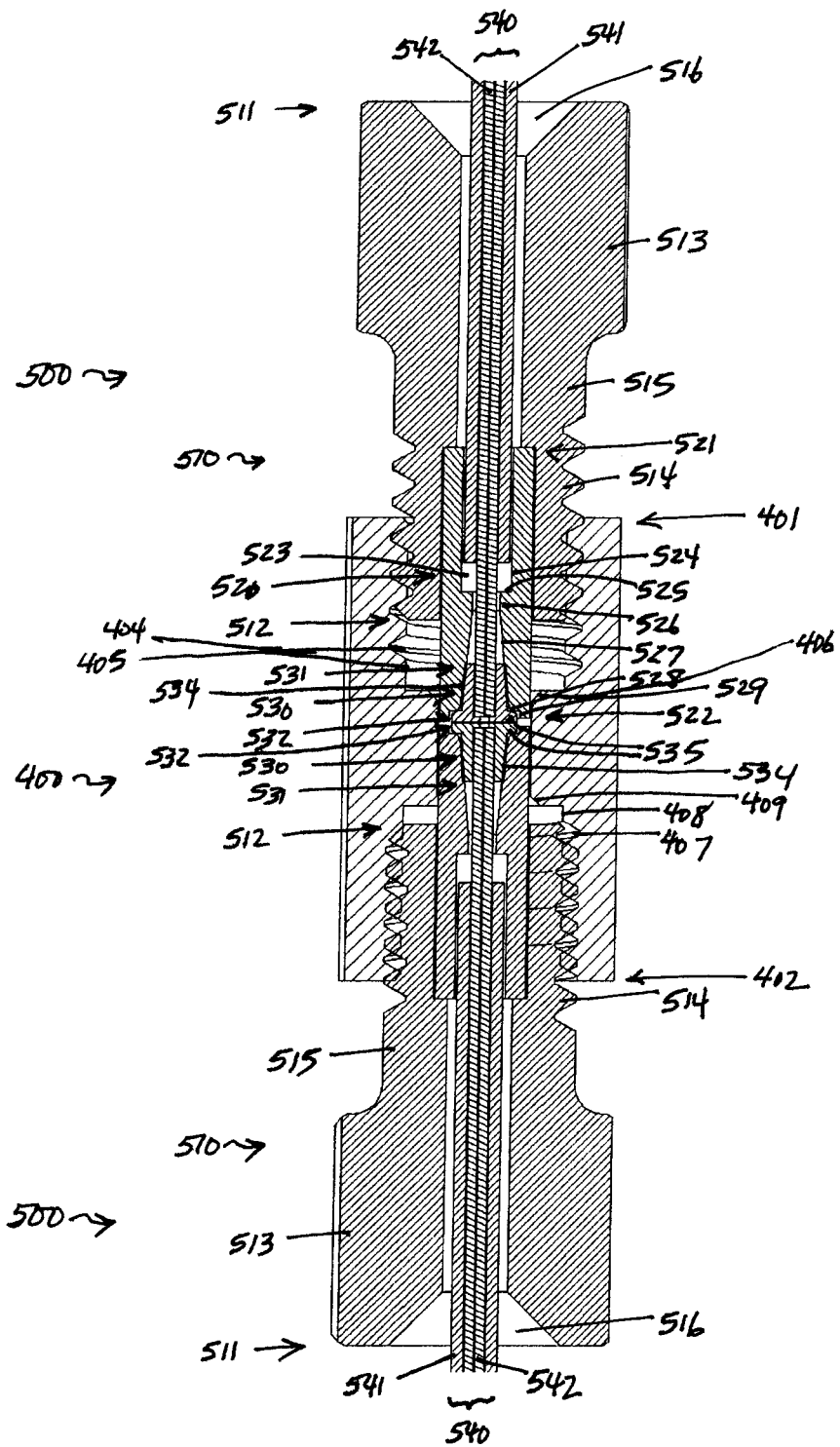
FIG. 29 is a cross-sectional view of the union and tube connection assemblies of FIG. 28 upon engagement.

FIG. 29 is a cross-sectional view of the union 400 and tube connection assemblies 500 of FIG. 28 upon engagement. Assemblies 500 each comprise a nut 510, locktube 520, ferrule 530 and tube 540. Nut 510 comprises first end 511 and second end 512, nut head 513, which is proximal to the first end 511 of the nut 510, an externally threaded portion 514 proximal to the other or second end 512 of the nut 510, externally non-threaded portion 515 between the nut head 513 and the externally threaded portion 514 and internal passageway 516 through the nut 510 from the first end 511 to the second end 512 of the nut 510, which broadens proximal the second end 512 to engage with locktube 520. Locktube 520 comprises a first end 521 and a second end 522, an internal passageway 523 that extends from the first end 521 to the second end 522 of the locktube 520, a first internal non-tapered portion 524, a first internal lip 525, a second internal non-tapered portion 526, an internal tapered portion 527, a second internal lip 528, and a third internal non-tapered portion 529. Ferrule 530 comprises a first end 531 and a second end 532, and defines an internal passageway (not visible in FIG. 29) that extends from the first end 531 to the second end 532 of the ferrule 530. Ferrule 530 also comprises an external tapered portion 534 and an optional protrusion 535 proximal the second end 532 of the ferrule 530. The external tapered portion 534 of the ferrule 530 forms a truncated conical shape. Tube 540 comprises a strain relief tube 541 and an inner tube 542. Union 400 comprises a first end 401 a second end 402, an internal passageway (not visible in FIG. 29) that extends from the first end 401 to the second end 402 of the union 400, a first internally threaded portion 404, a first internal non-tapered portion 405, and a first internal tapered portion 406 proximal to the first end 401 of the union 400, and a second internally threaded portion 407, a second internal non-tapered portion 408, and a second internal tapered portion 409 proximal to the second end 402 of the union 400.

Figure 30:
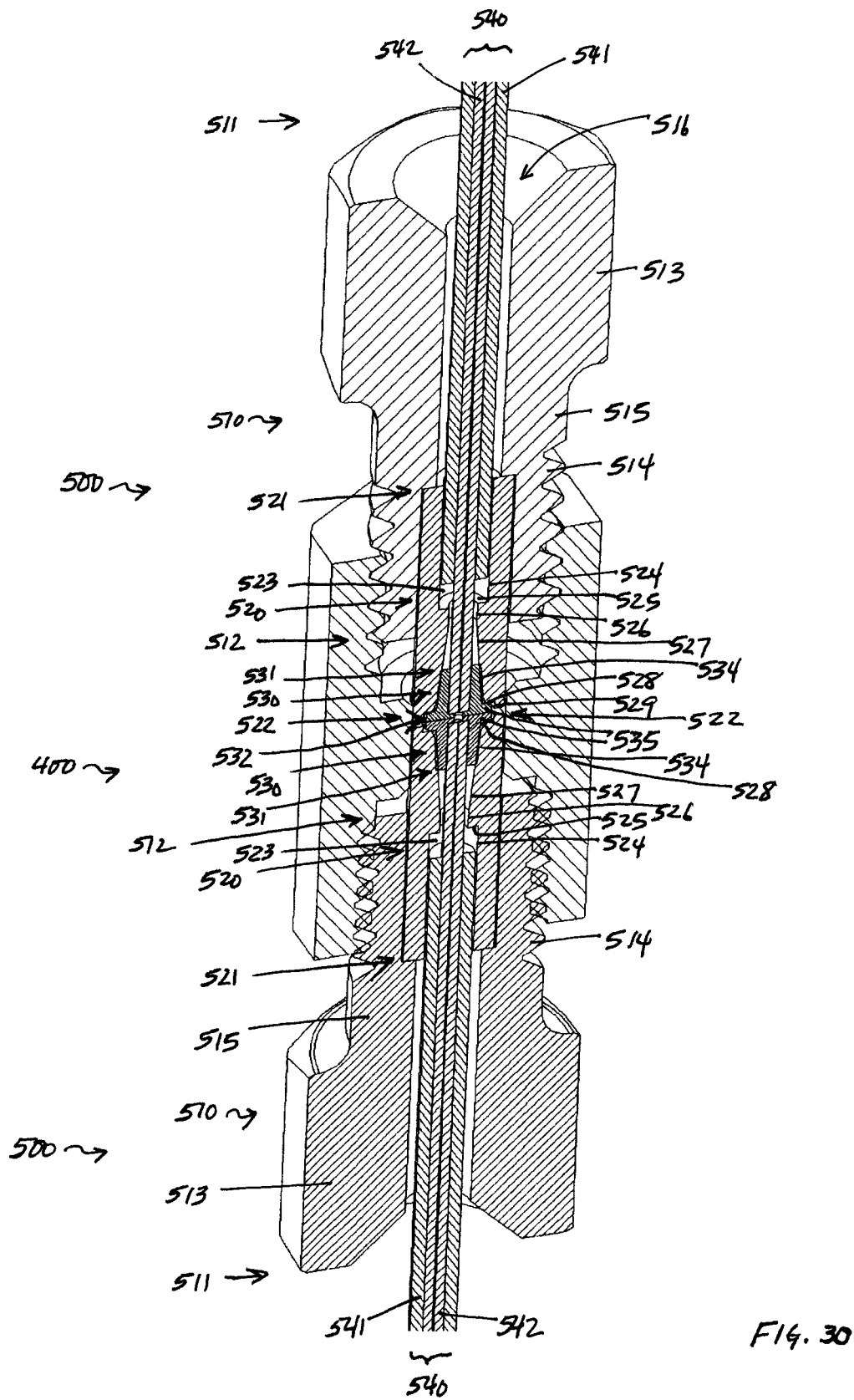
FIG. 30 is a top side perspective cross-sectional view of the union and tube connection assemblies of FIG. 28 upon engagement.

FIG. 30 is a top side perspective cross-sectional view of the union and tube connection assemblies of FIG. 28 upon engagement. Assemblies 500 each comprise a nut 510, locktube 520, ferrule 530 and tube 540. Nut 510 comprises first end 511 and second end 512, nut head 513, which is proximal to the first end 511 of the nut 510, an externally threaded portion 514 proximal to the other or second end 512 of the nut 510, externally non-threaded portion 515 between the nut head 513 and the externally threaded portion 514 and internal passageway 516 through the nut 510 from the first end 511 to the second end 512 of the nut 510, which broadens proximal the second end 512 to engage with locktube 520. Locktube 520 comprises a first end 521 and a second end 522, an internal passageway 523 that extends from the first end 521 to the second end 522 of the locktube 520, a first internal non-tapered portion 524, a first internal lip 525, a second internal non-tapered portion 526, an internal tapered portion 527, a second internal lip 528, and a third internal non-tapered portion 529. Ferrule 530 comprises a first end 531 and a second end 532, and defines an internal passageway (not visible in FIG. 30) that extends from the first end 531 to the second end 532 of the ferrule 530. Ferrule 530 also comprises an external tapered portion 534 and an optional protrusion 535 proximal the second end 532 of the ferrule 530. The external tapered portion 534 of the ferrule 530 forms a truncated conical shape. Tube 540 comprises a strain relief tube 541 and an inner tube 542. Union 400 comprises a first end 401 a second end 402, an internal passageway (not visible in FIG. 29) that extends from the first end 401 to the second end 402 of the union 400, a first internally threaded portion 404, a first internal non-tapered portion 405, and a first internal tapered portion 406 proximal to the first end 401 of the union 400, and a second internally threaded portion 407, a second internal non-tapered portion 408, and a second internal tapered portion 409 proximal to the second end 402 of the union 400.

As shown in FIG. 29 and FIG. 30, ferrules 530 of assemblies 500 are compressed together in union 400, which creates a seal. Therefore there is less dead volume since the ferrules 530 seal at or near the orifice (not shown) of the ferrules 500.

Figure 31:
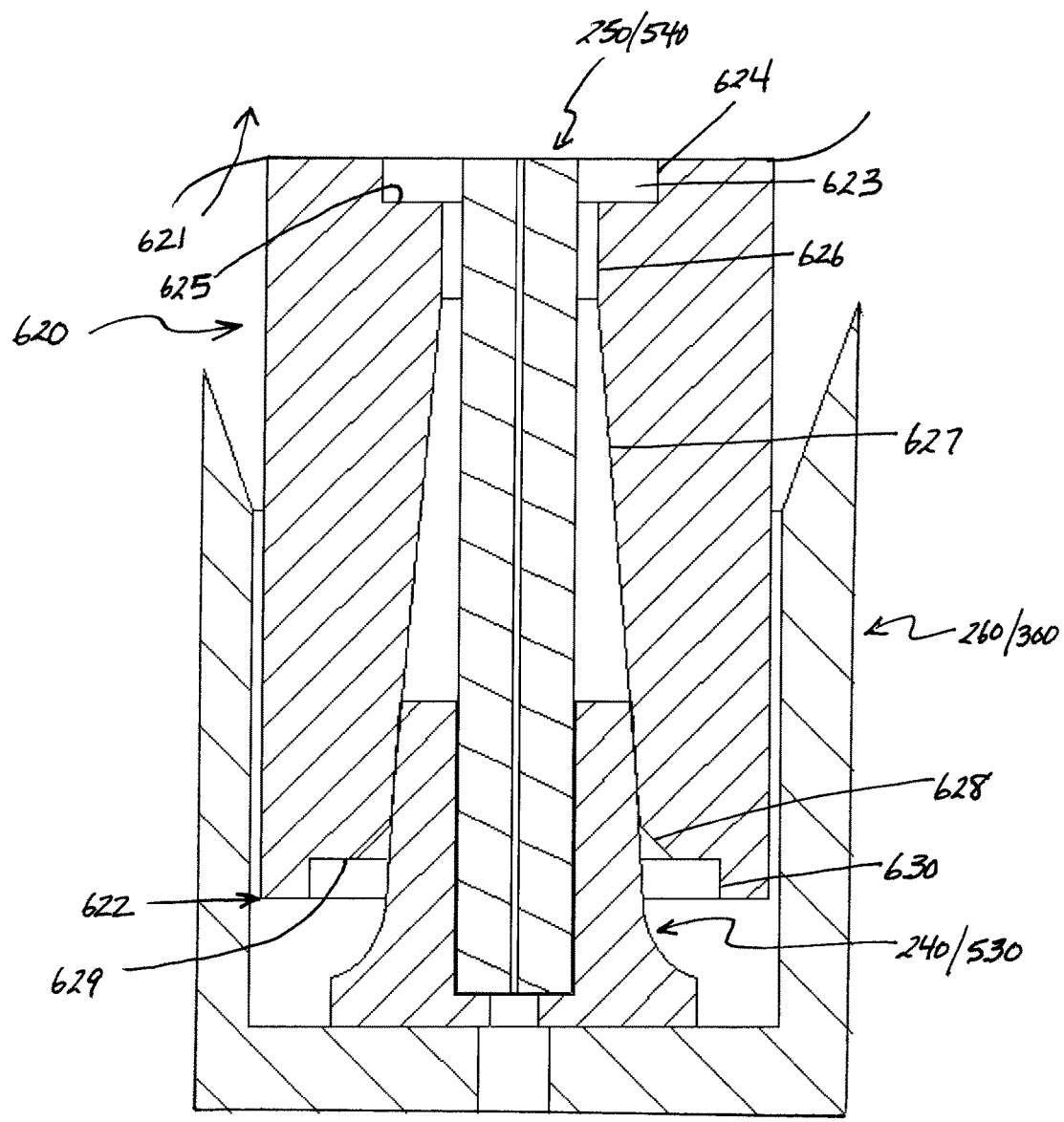
FIG. 31 is a cross sectional view of the lower portion of an alternative locktube for use with the tube connection assembly of FIG. 11 or FIG. 20.

FIG. 31 is a cross-sectional view of the lower portion of an alternative locktube 620 that can be used in connection assemblies 200 or 500. Locktube 620 comprises a first end (not visible in FIG. 31) and a second end 622, an internal passageway 623 that extends from the first end (not visible in FIG. 31) to the second end 622 of the locktube 620, a first internal non-tapered portion 624, a first internal lip 625, a second internal non-tapered portion 626, a first internal tapered portion 627, a second internal tapered portion 628, a second internal lip 629, and a third internal non-tapered portion 630. Also shown in FIG. 31 for clarity is a ferrule (which could be either 240 or 530, for example), lower portion of a tube (which could be either 250 or 540, for example) and lower portion of a port (which could be 260 or 300, for example).

It will be appreciated that the nut 510, washer 520, locktube 530 and ferrule 540 in connection assembly 500, as well as alternative locktube 620, can comprise a number of different materials. Nut 510, washer 520, locktube 530, ferrule 540, and locktube 620 can comprise a metal, such as stainless steel, or can comprise a polymer, such as a polyaryletherketone (PAEK), including, but not limited to, polyetherketone (PEK), polyetheretherketone (PEEK™), polyetherketoneketone (PEKK), polyetheretherketoneketone (PEEKK), and polyetherketoneetherketoneketone (PEKEKK). In addition, each of the components of the connection assembly 500 can comprise the same material, or some or all of the components can comprise different materials. It will be appreciated that a variety of metals and polymers may be selected for the components of the connection assembly 500 depending on the particular application, as that may involve a particular type of sample, a particular type of solvent, and/or a particular pressure range. In addition, the selection of materials for the tube 540, such as PEEK™, PEEKsil™, metal, including, but not limited to, stainless steel, titanium, nickel or gold, coated metal, or fused silica, may lead to a selection of a particular material for the components of the connection assembly 500. In addition, PEEK™ (or other polymers) may be used that is reinforced with carbon, carbon fibers, glass fibers, or steel fibers, or the like. Other polymer materials which may be used include, but are not limited to, TEFLON®, TEFZEL®, DELRIN®, polyphenylene sulfide (PPS), polypropylene, and others, depending on the foregoing factors and perhaps others, such as cost. Those skilled in the art will further appreciate that connection assembly 500 is shown for connecting tube 540 to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

The fittings and assemblies disclosed herein have been found through testing to meet a requirement of 18,000 psi plus a factor of safety reliably.

As shown herein, the internal tapered portions of the disclosed locktubes and the external tapered portions of the disclosed ferrules each define an angle from the axis of the disclosed locktubes and ferrules, respectively. However, those skilled in the art will appreciate that the internal tapered portions of the disclosed locktubes and external tapered portions of the disclosed ferrules can define different angles if desired, and can define angles that are about equal to each other, or differ from each other, depending upon the particular application, and in certain embodiments could be curved. In addition, although a single angle for each of the disclosed locktubes and the disclosed ferrules is shown herein, each can have multiple or differing angles in different portions thereof. Those skilled in the art will further appreciate that the externally threaded portions of the disclosed assemblies may be adapted so that they can be removably engaged with any sized port, union, fitting, or component of an LC or other AI system (not shown). The use of external threads on one element, such as the disclosed nuts, for example nut 510, versus internal threads, is a matter of selection. Those skilled in the art will therefore appreciate that, for example, the nut 510 in an alternative embodiment could have internal threads (not shown) located near a second end which could be engaged with external threads (not shown) located near the first end of an alternative embodiment of a port, union, fitting, or component of an LC or AI system (not shown).

It will be appreciated that the various components of the disclosed assemblies can comprise a number of different materials, such as a metal, such as stainless steel, or can comprise a polymer, such as a polyaryletherketone (PAEK), including, but not limited to, polyetherketone (PEK), polyetheretherketone (PEEK™), polyetherketoneketone (PEKK), polyetheretherketoneketone (PEEKK), and polyetherketoneetherketoneketone (PEKEKK). In addition, each of the components of the disclosed assemblies can comprise the same material, or some or all of the components can comprise different materials. It will be appreciated that a variety of metals and polymers may be selected for the components of the disclosed assemblies depending on the particular application, as that may involve a particular type of sample, a particular type of solvent, and/or a particular pressure range. In addition, the selection of materials for the disclosed tubes, such as PEEK™, PEEKsil™, metal, including, but not limited to, stainless steel, titanium, nickel or gold, coated metal, or fused silica, may lead to a selection of a particular material for the components of the disclosed assemblies. In addition, PEEK™ (or other polymers) may be used that is reinforced with carbon, carbon fibers, glass fibers, or steel fibers, or the like. Other polymer materials which may be used include, but are not limited to, TEFLON®, TEFZEL®, DELRIN®, polyphenylene sulfide (PPS), polypropylene, and others, depending on the foregoing factors and perhaps others, such as cost. Those skilled in the art will further appreciate that the disclosed assemblies are shown for connecting the disclosed tubes to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

While the present invention has been shown and described in various embodiments, those skilled in the art will appreciate from the drawings and the foregoing discussion that various changes, modifications, and variations may be made without departing from the spirit and scope of the invention as set forth in the claims. Hence the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

We claim:

1. A connection assembly for use in an analytical instrument system, comprising:
   a) a nut having a first end and a second end and a passageway therethrough, a nut head proximal to said first end of the nut, an externally non-threaded portion, and an externally threaded portion;
   b) a locktube having a first end and a second end and a passageway therethrough, at least a first internal non-tapered portion proximal the first end of the locktube and an internal tapered portion proximal the second end of the locktube, said first end of said locktube adapted to engage said second end of said nut; and
   c) a ferrule having a first end, a second end, a passageway therethrough, and an external tapered portion proximal the first end of the ferrule, wherein said external tapered portion of said ferrule is adapted to securely engage with said internal tapered portion of said locktube; and wherein the second end of the ferrule has an external protrusion with an outer diameter greater than the external tapered portion of the ferrule and wherein the second end of the ferrule is adapted to securely engage with a flat-bottomed port.

2. The connection assembly according to claim 1, further comprising a washer between said nut and said locktube, said washer having a passageway therethrough.

3. The connection assembly according to claim 1, wherein said nut head is a hexagonal nut head.

4. The connection assembly according to claim 1, wherein said nut head is a knurled nut head.

5. The connection assembly according to claim 1, wherein said nut head comprises a plurality of splines.

6. The connection assembly of claim 1, wherein the angle of said internal tapered portion of said locktube comprises an included angle between 3° and 12°.

7. The connection assembly of claim 6, wherein the angle of the internal tapered portion of said locktuhe is about 6°.

8. The connection assembly of claim 1, wherein the external tapered portion of said ferrule comprises an included angle between 2° and 11°.

9. The connection assembly of claim 8, wherein the angle of the external tapered portion of the ferrule is 4°.

10. The connection assembly according to claim 1, wherein the internal tapered portion of the locktube and the external tapered portion of the ferrule comprise equal included angles.

11. The connection assembly of claim 1, wherein said locktube further comprises at least a second lip and at least a third non-tapered portion proximal to said second end of said locktube.

12. The connection assembly of claim 11, wherein the internal tapered portion of the locktube comprises an included angle between 4° and 14°.

13. The connection assembly of claim 12, wherein the internal tapered portion of the locktube comprises an included angle of 10°.

14. The connection assembly of claim 1, wherein said ferrule furrther comprises:
   a) an external radius between said external tapered portion and said external protrusion, and;
   b) an internal lip.

15. The connection assembly of claim 14, wherein external tapered portion of the ferrule comprises an included angle between 2° and 12°.

16. The connection assembly of claim 15, wherein the external tapered portion of the ferrule comprises an included angle of 8°.

17. The connection assembly according to claim 14, wherein the internal tapered portion of the locktube and the external tapered portion of the ferrule comprise equal included angles.

18. The connection assembly according to claim 1, wherein said nut, said locktube or said ferrule comprises polyetheretherketone.

19. The connection assembly according to claim 1, further comprising at least one tube extending at least partially through the passageways of the nut, the locktube and the ferrule.

20. The connection assembly according to claim 19, wherein said ferrule contacts said tube without substantially deforming the tube.

21. The connection assembly according to claim 1, wherein at least a portion of the nut, the locktube or the ferrule is biocompatible.

22. A tube assembly for use in an analytical instrument system, comprising:
   a) nut having a first end and a second end and a passageway therethrough, a nut head proximal to said first end of the nut, an externally non-threaded portion, and an externally threaded portion;
   b) a locktube having a first end and a second end and a passageway therethrough, an internal non-tapered portion proximal the first end of the locktube and an internal tapered portion proximal the second end of the locktube, said first end of said locktube adapted to engage said second end of said nut;
   c) a ferrule having a first end, a second end, a passageway therethrough, and an external tapered portion proximal the first end of the ferrule, wherein said external tapered portion of said ferrule is adapted to securely engage with said internal tapered portion of said locktube, and wherein the second end of the ferrule extends beyond the second end of the locktube when the ferrule and the locktnbe are securely mailed, and wherein the second end of the ferrule is adapted to securely engage with a flat-bottomed port; and
   d) a tube located in the passageways of said nut, said locktube and said ferrule.

23. The tube assembly according to claim 22, further comprising a washer between said nut and said locktube, said washer defining a passageway therethrough.

24. The tube assembly according to claim 22, wherein said ferrule further comprises an external protrusion proximal the second end of said ferrule.

25. The tube assembly according to claim 22, wherein said tube comprises a metal, a polymer, fused silica, or a combination thereof.

26. The tube assembly according to claim 25, wherein said tube comprises a metal.

27. The tube assembly according to claim 26, wherein said tube comprises stainless steel.

28. The tube assembly according to claim 25, wherein said tube comprises a polymer.

29. The tube assembly of claim 28, wherein said tube comprises polyetheretherketone.

30. The tube assembly according to claim 25, wherein said tube comprises fused silica.

31. The tube assembly according to claim 22, wherein at least a portion of the nut, the locktube or the ferrule is biocompatible.

* * * * *